US011460473B2

United States Patent
Gougeon et al.

(10) Patent No.: US 11,460,473 B2
(45) Date of Patent: Oct. 4, 2022

(54) ASSAY TO DETECT AND QUANTITATE SPECIFIC AN ANTIBODIES FOR VARIOUS REDOX FORMS OF HMGB1

(71) Applicant: INSTITUT PASTEUR, Paris (FR)

(72) Inventors: Marie-Lise Gougeon, Antony (FR); Nicole Prada, Paris (FR); Hela Saidi, Villejuif (FR)

(73) Assignee: INSTITUT PASTEUR, Paris (FR)

( * ) Notice: Subject to any disclaimer, the term of this patent is extended or adjusted under 35 U.S.C. 154(b) by 589 days.

(21) Appl. No.: 15/771,182

(22) PCT Filed: Nov. 3, 2016

(86) PCT No.: PCT/EP2016/076607
§ 371 (c)(1),
(2) Date: Apr. 27, 2018

(87) PCT Pub. No.: WO2017/077001
PCT Pub. Date: May 11, 2017

(65) Prior Publication Data
US 2018/0313848 A1 Nov. 1, 2018

(30) Foreign Application Priority Data
Nov. 3, 2015 (EP) .................................... 15306747

(51) Int. Cl.
*G01N 33/53* (2006.01)
*G01N 33/68* (2006.01)

(52) U.S. Cl.
CPC . *G01N 33/6854* (2013.01); *G01N 2333/4703* (2013.01); *G01N 2800/24* (2013.01); *G01N 2800/26* (2013.01); *G01N 2800/28* (2013.01); *G01N 2800/2814* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| 8,450,076 | B2 | 5/2013 | Gougeon et al. |
| 8,603,766 | B2 | 12/2013 | Gougeon et al. |
| 8,728,748 | B2 | 5/2014 | Gougeon et al. |
| 8,906,634 | B2 | 12/2014 | Gougeon et al. |
| 9,164,103 | B2 | 10/2015 | Gougeon et al. |
| 9,164,107 | B2 | 10/2015 | Gougeon et al. |
| 9,766,254 | B2 | 9/2017 | Gougeon et al. |
| 10,012,655 | B2 | 7/2018 | Gougeon et al. |

FOREIGN PATENT DOCUMENTS

| WO | 2010/029164 A1 | 3/2010 |
| WO | 2011/110650 A2 | 9/2011 |

OTHER PUBLICATIONS

Venereau et al., Mutually exclusive redox forms of HMGB1 promote cell recruitment or proinflammatory cytokine release, The Journal of Experimental Medicine, 2012, vol. 209, No. 9, pp. 1519-1528. (Year: 2012).*
Barnay-Verdier et al., Emergence of autoantibodies to HMGB1 is associated with survival in patients with septic shock, Intensive Care Med, 2011, 37, pp. 957-962. (Year: 2011).*
Venereau et al., Mutually exclusive redox forms of HMGB1 promote cell recruitment or proinflammatory cytokine release, J. Ex. Med., 2012, vol. 209, No. 9, pp. 1519-1528. (Year: 2012).*
Urbonaviciute et al., Factors masking HMGB1 in human serum and plasma, Journal of Leukocyte Biology, vol. 81, Jan. 2007, pp. 67-74. (Year: 2007).*
Li et al., Improvement of a low pH antigen-antibody dissociation procedure for ELISA measurement of circulating anti-AB antibodies, BMC Neuroscience, Mar. 2007, 8:22, pp. 1-11 (Year: 2007).*
Lederman et al. "A single amino acid substitution in a common African allele of the CD4 molecule ablates binding of the monoclonal antibody, OKT4" Mol Immunol. Nov. 1991;28(11): pp. 1171-1181. (Year: 1991).*
Harlow, E. and Lan D., Antibodies: A Laboratory Manual (1988) Cold Spring Harbor Laboratory Press, Cold Spring Harbor, NY, pp. 23-26 (Year: 1988).*
Colman et al. Research im Immunology, 1994; 145(1):pages 33-36. (Year: 1994).*
Venereau E. et al.: "DAMPs from cell death to new life", Frontiers Immunol., vol. 6, 422, Aug. 18, 2015 (Aug. 18, 2015), pp. 1-11.
Magna M. et al.: "The role of HMGBI in the pathogenesis of inflammatory and autoimmune diseases", Mol. Med., vol. 20, No. 1, Mar. 24, 2014 {Mar. 24, 2014), pp. 138-146.
Antoine D.J. et al.: "A systematic nomenclature for the redox states of high mobility group box (HMGB) proteins", Mol. Med., vol. 20, No. 1, Mar. 24, 2014 {Mar. 24, 2014), pp. 135-137.
Tang D. et al.: "A Janus tale of two active high mobility group box 1 (HMGBI) redox states", Mol. Med., vol. 18, Dec. 20, 2012 (Dec. 20, 2012), pp. 1360-1362.
Yang H. et al.: "High Mobility Group Box Protein 1 (HMGBI): The prototypical endogenous danger molecule", Mol. Med., vol. 21, No. Suppl 1, Jan. 1, 2015 (Jan. 1, 2015), pp. S6-S12.
Gougeon M.-L. et al.: "HMGBI, an alarmin promoting HIV dissemination and latency in dendritic cells", Cell Death Differ., vol. 19, No. 1, Jan. 2012 (Jan. 2012), pp. 96-106.

(Continued)

*Primary Examiner* — Gary Counts
(74) *Attorney, Agent, or Firm* — Arrigo, Lee, Guttman & Mouta-Bellum LLP

(57) ABSTRACT

Quantitation of specific antibodies for at least one redox form of High mobility group box 1 (HMGB1) contained in a biological sample. An in vitro method for assessing the state of progression of a disease or a disorder in which HMGB1 is involved. An in vitro method for the identification of predisposition, prognostic or diagnostic biomarkers of a disease or a disorder in which HMGB1 is involved. A kit to quantitate said specific antibodies for at least one redox form of HMGB1.

10 Claims, 18 Drawing Sheets

(56) References Cited

OTHER PUBLICATIONS

Gougeon M.-L.: "Alarmins and central nervous system inflammation in HIV-associated neurological disorders", J. Intern. Med., 12570, Nov. 16, 2016 (Nov. 16, 2016), pp. 1-15.
International Search Report, PCT/EP2016/076607, dated Dec. 13, 2016.

* cited by examiner

| Redox status | All-thiol | Disulfide | Oxidized |
|---|---|---|---|
| Structure | $-C_{23}-C_{45}-C_{106}-$<br>$\phantom{-}|\phantom{xx}|\phantom{xx}|$<br>SH  SH  SH | $-C_{23}-C_{45}-C_{106}-$<br>$\phantom{-}|\phantom{xx}|\phantom{xx}|$<br>S—S   SH | $-C_{23}-C_{45}-C_{106}-$<br>$\phantom{-}|\phantom{xx}|\phantom{xx}|$<br>SO$_3$H SO$_3$H SO$_3$H |
| Activity | Chemoattractant activity | Cytokine-inducing activity | Nonimmune activity |

Figure 1

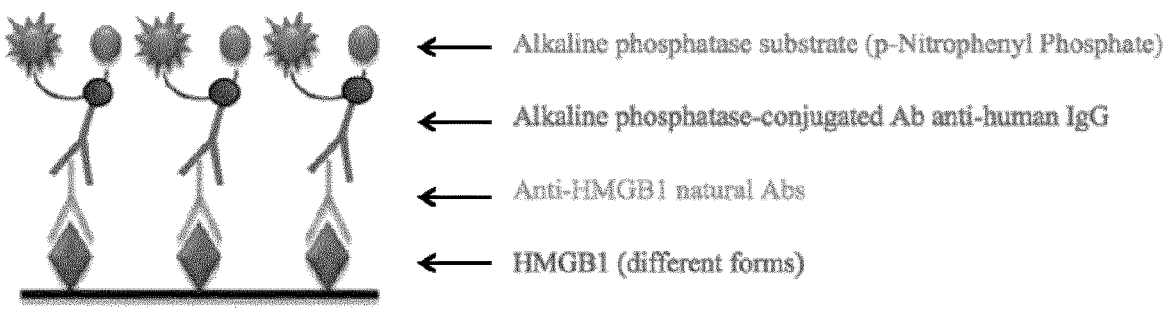

← Alkaline phosphatase substrate (p-Nitrophenyl Phosphate)

← Alkaline phosphatase-conjugated Ab anti-human IgG

← Anti-HMGB1 natural Abs

← HMGB1 (different forms)

| | Internal control | | | | |
|---|---|---|---|---|---|
| Exp | Meas. | Conc. | Mean | SD | CV |
| 1 | 0,408 | 402 | 402 | | |
| 2 | 0,454 | 451 | 427 | 22 | 5,19% |
| | 0,444 | 440 | | | |
| | 0,422 | 417 | | | |
| | 0,408 | 402 | | | |
| 3 | 0,281 | 488 | 479 | 9 | 1,85% |
| | 0,271 | 472 | | | |
| | 0,279 | 485 | | | |
| | 0,270 | 471 | | | |
| 4 | 0,258 | 404 | 434 | 22 | 5,10% |
| | 0,278 | 431 | | | |
| | 0,290 | 448 | | | |
| | 0,293 | 452 | | | |
| 5 | 0,378 | 560 | 567 | 9 | 1,58% |
| | 0,378 | 560 | | | |
| | 0,391 | 579 | | | |
| | 0,385 | 570 | | | |
| 6 | 0,608 | 335 | 323 | 17 | 5,29% |
| | 0,562 | 311 | | | |
| Between exp | 0,371 | 457 | 439 | 81 | 18,54% |

ASSAY TO DETECT AND QUANTITATE SPECIFIC AN ANTIBODIES FOR VARIOUS REDOX FORMS OF HMGB1

The invention relates to the quantitation of specific antibodies for at least one redox form of High mobility group box 1 (HMGB1) contained in a biological sample, in particular human serum and/or CerebroSpinal Fluid (CSF). The invention also relates to an in vitro method for assessing the state of progression of a disease or a disorder in which HMGB1 is involved, to an in vitro method for the identification of predisposition, prognostic or diagnostic biomarkers of a disease or a disorder in which HMGB1 is involved. The invention also relates to a kit to quantitate said specific antibodies for at least one redox form of HMGB1, in particular human HMGB1.

HMGB1 is among the most important chromatin proteins. In the nucleus, HMGB1 interacts with nucleosomes, transcription factors, and histones. HMGB1 is secreted by immune cells (like macrophages, monocytes and dendritic cells (DCs)) and it acts as a cytokine mediator of inflammation (Wang H, et al. *Science*, 1999, 285 (5425): 248-251). Antibodies that neutralize HMGB1 confer protection against damage and tissue injury during arthritis, sepsis, and Systemic Lupus Erythematosus (SLE). It has also been discovered that HMGB1 may be involved in evolution of infectious diseases, in particular HMGB1 triggers HIV-replication in HIV-infected DCs (Saidi H, et al. *PLoS One* 2008), and also upregulates two potent apoptosis inhibitors in HIV-infected DCs, c-IAP2 and c-FLIP, rendering them resistant to the killing activity of natural killer (NK) cells (Melki M-T et al. *PLoS Pathogens* 2010, 6(4): e1000862), thus contributing to the constitution of viral reservoirs in DCs.

Recent findings have reported the quantitation of HMGB1 in sera from HIV-infected patients at different stages of HIV disease, and an Enzyme-Linked Immunosorbent Assay (ELISA assay) for the detection of anti-HMGB1 antibodies in patients' fluids applied for the identification of correlates of disease evolution has also been disclosed (international patent applications WO2010/029164 and WO2011/110650). HMGB1, in addition to IP-10 and MCP-1, has been detected in CerebroSpinal Fluid (CSF) from HIV-infected patients with HIV-associated neurological disorders (HAND), and these mediators represented a correlate of viral replication and disease evolution. Moreover, the persistence of anti-HMGB1 antibodies in CSF from patients with suppressed viral replication was found to be a determinant of HAND.

In particular, international patent application WO2010/029164 relates to diagnostic and prognostic methods involving measuring HMGB1 levels and/or specific antibodies for HMGB1 as well as antibody- and drug-based methods for treating or reducing the severity of HIV infection by modulating the activity of HMGB1.

In particular, international patent application WO2011/110650 relates to the quantitation of the protein HMGB1 or of the specific antibodies for HMGB1 in a biological sample, in particular serum and CSF, and their respective correlation with prognostic methods of the state of progression of neurological disorders or toward neurological disorders, in particular neurological disorders associated with HIV infection and with diagnostic methods. This patent application also relates to the correlation of the protein HMGB1 or of the specific antibodies for HMGB1 with the monitoring of HIV infection or with viral load as well as prognostic methods of the state of progression of AIDS.

In an attempt to further assess HMGB1 activities, attention was drawn to its various chemical forms, in particular to its redox forms. HMGB1 contains three cysteine residues at positions 23, 45, and 106, which are sensitive to redox-dependent modifications (Venereau et al. *JEM* 2012, 209(9), 1519-1528; Tang et al. *Mol Med* 2012, 18: 1360-1362; Bianchi et al., *JLB* 2009, 86, 573-576; Schiraldi et al., *JEM* 2012, 209(3), 551-563). Recent findings demonstrate that redox and acetyl modifications directly control cytokine and chemotactic activities of HMGB1. The cytokine activity of HMGB1 depends on C23-C45 disulfide bond within the first HMG-box domain of HMGB1, BoxA, whereas the unpaired C106 within Box B must be in the thiol state (Yang et al. *Mol Med* 2012, 18: 250-259). Both terminal oxidation of these cysteines to sulfonates ($CysSO_3^-$) with reactive oxygen species (ROS) and their complete reduction to thiols (CySSH) abrogate the cytokine-stimulating activity. It was also found that only the fully reduced form of HMGB1, where all three cysteines are in the thiol state, can recruit motile cells, thus exhibiting a chemokine activity. Therefore, reduced cysteines make HMGB1 a chemoattractant, whereas a disulfide bond makes it a proinflammatory cytokine, and further cysteine oxidation to sulfonates by ROS abrogates both activities (FIG. 1).

HMGB1 is a well-known protein appearing in the nucleus and is also known to be a cytokine. Physical and functional characteristics of HMGB1 are disclosed by and incorporated by reference to Lotze, et al. (Nature Reviews, Immunology, 2005, 5:351).

In view of available data showing that expression of at least one redox form of HMGB1 protein is related to the in vivo activities of the protein, the inventors have conceived an interest for the design of means and methods that would enable to detect the expression of specific antibodies for at least one of said redox forms, in particular in a context of assaying biological samples obtained from patients suffering from inflammatory or infectious diseases. More particularly, the inventors have made the hypothesis that in vivo expression of at least one redox form of HMGB1 protein may be associated with elicitation in a patient of anti-HMGB1 antibodies directed against a redox form (i.e. specific antibodies for one redox form) and that the determination of these antibodies having recognition capacity for one redox form of the HMGB1 protein or their quantitation in a biological sample would be of interest in the assessment of a patient's status and condition. The present invention describes an assay that allows detecting and quantifying the levels of specific antibodies for at least one redox form of HMGB1 in a biological sample, in particular in a human serum and/or CSF, obtained from a subject.

The present invention relates to an in vitro method for quantitating specific antibodies for at least one redox form of High mobility group box 1 (HMGB1) contained in a biological sample obtained from a subject, comprising:

a) contacting said biological sample with at least one redox form of HMGB1 or HMGB1 derivatives as long as these derivatives bind to specific antibodies for at least one redox form of HMGB1; and b) quantitating the specific antibodies for at least one redox form of HMGB1;

wherein the redox form of HMGB1 is selected from the group of fully reduced HMGB1, disulfide-HMGB1 and oxidized-HMGB1.

The expression "specific antibodies for at least one" redox form of HMGB1 thus defines the possibility to perform the method in order to detect one, two or three types of antibodies wherein each type of antibodies is specific for one redox form of HMGB1.

In the context of the invention, the term "specifically" or "specific" relating to the antibodies means that the antibodies of the invention or their fragments are able to recognize and bind one redox form of HMGB1 from the group of fully reduced HMGB1, disulfide-HMGB1 and oxidized-HMGB1, and do not significantly recognize and bind other cellular proteins, i.e. cellular proteins distinct from said redox forms of HMGB1.

The present invention thus relates to an in vitro method for quantitating (a) specific antibodies for fully reduced HMGB1, or (b) specific antibodies for disulfide-HMGB1, or (c) specific antibodies for oxidized-HMGB1, or (d) specific antibodies for fully reduced HMGB1 and specific antibodies for disulfide-HMGB1, or (e) specific antibodies for fully reduced HMGB1 and specific antibodies for oxidized-HMGB1, or (f) specific antibodies for disulfide-HMGB1 and specific antibodies for oxidized-HMGB1, or (g) specific antibodies for fully reduced HMGB1 and specific antibodies for disulfide-HMGB1 and specific antibodies for oxidized-HMGB1, contained in a biological sample obtained from a subject, comprising:

a) contacting said biological sample with at least one redox form of HMGB1 selected from the group of fully reduced HMGB1, disulfide-HMGB1 and oxidized-HMGB1 or HMGB1 derivatives as long as these derivatives bind to said specific antibodies; and b) quantitating said specific antibodies of (a) to (g).

According to the invention, fully reduced HMGB1, also named all-thiol-HMGB1, corresponds to HMGB1 in which all three cysteine residues at positions 23, 45 and 106 have been completely reduced to thiols. Disulfide-HMGB1 has a disulfide bridge between cysteine residues at positions 23 and 45 (C23-C45 disulfide bond) and a reduced cysteine residue at position 106 (C106 thiol). Oxidized-HMGB1 (abbreviated as Ox) corresponds to HMGB1 in which the three cysteine residues at positions 23, 45 and 106 have been oxidized to sulfonates. Non-oxidizable chemokine-HMGB1 (abbreviated as Non-Ox) is a mutant protein where all cysteine residues at positions 23, 45 and 106 have been replaced by serine residues, thus being resistant to inactivation by ROS.

In a particular embodiment of the invention, the in vitro method of the invention may also comprise before the step of contacting the biological sample with at least one redox form of HMGB1 or HMGB1 derivatives (as long as these derivatives bind to specific antibodies for at least one redox of HMGB1), i.e. before step a), a step of treating the biological sample by an acid solution to dissociate the immune complexes found in the sample, preferably treating said biological sample with a Glycine solution at a low pH. When said acid treatment is carried out, the quantitated specific antibodies for at least one redox form of HMGB1 are total specific antibodies for at least one redox form of HMGB1.

In a particular embodiment of the invention, the acid dissociation solution is a Glycine solution (e.g. 1.5M) at a low pH, preferably between pH 1 and 3 (e.g. 1.85). The acid treatment is then stopped with a neutralization buffer (such as Tris, for example 1.5M Tris, pH 9). The acid treatment leads to a dilution of the biological sample. In another preferred embodiment, in combination with the previous one or not, the incubation with the acid dissociation solution is carried out at a temperature between 20 and 37° C., preferably at 25° C., and/or the neutralization step takes place in ice. In a particular embodiment of the invention, the in vitro method of the invention is based on (encompasses) the quantitation of the circulating fraction of specific antibodies for at least one redox form of HMGB1 (so-called circulating antibodies or residual antibodies) and/or their immunologically complexed fraction.

The quantitation of total specific antibodies for at least one redox form of HMGB1 may be preferred.

When the quantitation is based on total specific antibodies for at least one redox form of HMGB1, the method of the invention also comprises a step suitable for dissociation of immunological complexes formed between HMGB1 and HMGB1-specific antibodies, based on the acid treatment as disclosed above. When the quantitation is based on circulating specific antibodies for at least one redox form of HMGB1, said dissociation step is not required.

In the present application, the term "quantitating" encompasses the term "quantifying" and any suitable informative determination of specific antibodies for at least one redox form of HMGB1.

According to an embodiment of the invention, each type of antibodies recognizing a particular redox form of HMGB1 is determined quantitatively. In a particular embodiment, the method for quantitating specific antibodies for at least one redox form of HMGB1 is used to assess the prevalence of the specific antibodies for a given redox form.

In a particular embodiment of the invention, the in vitro method allows for quantitation of specific antibodies for one or at least one redox form of HMGB1, i.e. fully reduced HMGB1, or disulfide-HMGB1, or oxidized-HMGB1.

In a preferred embodiment, the in vitro method allows for quantitation of specific antibodies for oxidized-HMGB1.

In another particular embodiment of the invention, the in vitro method allows for quantitation of specific antibodies for two or at least two redox forms of HMGB1, i.e. fully reduced HMGB1 and disulfide-HMGB1, or fully reduced HMGB1 and oxidized-HMGB1, or disulfide-HMGB1 and oxidized-HMGB1.

In another preferred embodiment, the in vitro method allows for quantitation of specific antibodies for oxidized-HMGB1 and quantitation of specific antibodies for another redox form of HMGB1 selected from fully reduced HMGB1 or disulfide-HMGB1, i.e. quantitation of specific antibodies for fully reduced HMGB1 and oxidized-HMGB1, or disulfide-HMGB1 and oxidized-HMGB1.

In another particular embodiment of the invention, the in vitro method allows for quantitation of specific antibodies for the three redox forms of HMGB1, i.e. fully reduced HMGB1 and disulfide-HMGB1 and oxidized-HMGB1.

According to these embodiments, the antibodies of each type or population (defined by reference to recognition capacity) are quantitated individually.

In a preferred embodiment, the in vitro method comprises individually quantitating specific antibodies for fully reduced HMGB1 and oxidized-HMGB1, or specific antibodies for disulfide-HMGB1 and oxidized-HMGB1.

By "circulating antibodies", it is meant the residual antibodies found in the biological sample, in particular in blood, plasma, serum, saliva, peripheral blood mononuclear cells (PBMCs) or PBMC supernatant, CerebroSpinal Fluid (CSF) or other body fluids or tissues, i.e., the antibodies that are found in a non-complexed form (with the different redox forms of HMGB1). The term "circulating" also applies to the residual antibodies against different redox forms of HMGB1 quantitated without acid treatment.

By "total antibodies", it is meant the sum or combined amount of circulating antibodies and immunologically complexed antibodies.

In a particular embodiment of the invention, said quantitation of specific antibodies for at least one redox form of HMGB1 is carried out by contacting in vitro a biological sample obtained from a subject, with at least one redox form of HMGB1 or derivatives thereof selected from the above defined groups of redox forms of HMGB1.

As an illustration, said quantitation is carried out using disulfide HMGB1 (HMGBiotech, HM-122), and/or fully reduced HMGB1 (HMGBiotech, HM-116) and/or non-oxidizable chemokine-HMGB1 (HMGBiotech, HM-132), disulfide HMGB1 (Proteogenix), fully reduced HMGB1 (Proteogenix), oxidized HMGB1 obtained adding $H_2O_2$ to the disulfide HMGB1, or any peptide (10 to 30 amino acid residues) or polypeptide (30 to 215 amino acid residues, preferably 30 to 50, or 30 to 100, or 30 to 150 residues) derived from HMGB1 (HMGB1 derivatives) as long as these derivatives bind to specific antibodies for at least one redox form of HMGB1 and/or enable to s quantitate specific antibodies for at least one redox form of HMGB1. Such derivatives are selected in the group consisting of a recombinant HMGB1, an immunologically reactive part of HMGB1, an immunologically reactive part of HMGB1 whose sequence is common to HMGB1 proteins of various origins.

The in vitro method of the invention optionally further comprises the quantitation of other molecules found in the biological sample (such as the serum or the cerebrospinal fluid sample), and in particular of chemokines. Examples of species of chemokines that can, independently, be assayed and quantitated, are IL-1β, IL-2, IL-4, IL-5, IL-6, IL-7, IL-8, IL-9, IL-10, IL-12 p70, IL-13, IL-15, IL-17, basic FGF, G-CSF, GM-CSF, IFN-γ, IP10, MCP1, MIP-1α, MIP-1β, PDGF-BB, RANTES, TNF-α GM-CSF, VEGF, in particular the chemokine IP-10 and the chemokine MCP-1. The human chemokine IP-10 (10 kDa interferon-gamma-induced protein) is also called Chemokine (C-X-C motif) ligand 10 or CXCL10, and is referenced under NCBI Accession Number NP_001556); the human chemokine MCP-1 (for monocyte chemotactic protein-1) is also called Chemokine (C-C motif) ligand 2 (CCL2) and is referenced under NCBI Accession Number NP_002973).

When applied to the molecules and in particular to the chemokines such as the chemokine IP-10 and the chemokine MCP-1, the term "quantitating" or "quantitation" encompasses the term "quantifying" and any suitable informative determination of the level of chemokine IP-10 and chemokine MCP-1.

In a particular embodiment of the invention, said at least one redox form of HMGB1 has a mammalian origin, preferably a human origin.

In a particular embodiment of the invention, said biological sample is blood, plasma, serum, saliva, peripheral blood mononuclear cells (PBMCs) or PBMC supernatant, CerebroSpinal Fluid (CSF) or other body fluids or tissues, preferably serum and/or CSF, more preferably human serum and/or CSF.

In a preferred embodiment, said subject is a human being, in particular a patient under diagnosis or under therapy.

The in vitro method of the invention may comprise a step of treating fully reduced HMGB1 to stabilize or obtain the reduced state of HMGB1, said treatment encompassing adding a reducing agent such as dithiothreitol (DTT), β-mercaptoethanol, TCEP (tris(2-carboxyl)phosphine), in particular DTT, preferably 0.5 mM DTT, to fully reduced HMGB1.

The in vitro method of the invention may also comprise a step of treating disulfide-HMGB1 to obtain oxidized-HMGB1, said treatment encompassing adding reactive oxygen species (ROS) such as hydroxyl radical (.OH), hydrogen peroxide ($H_2O_2$), superoxide radical ($O_2^-$), oxygen ($O_2$) and singlet oxygen ($^1O_2$), in particular hydrogen peroxide ($H_2O_2$), preferably 100 mM $H_2O_2$, to disulfide-HMGB1.

In the in vitro method of the invention, said biological sample is diluted from 1/800 to 1/2000, preferably at 1/1000.

The in vitro method of the invention may be carried out by implementing ELISA, or other immunological detection methods, using at least one redox form of HMGB1 or derivatives thereof as long as these derivatives bind to specific antibodies for at least one redox form of HMGB1 coated on a solid support, and optionally using secondary antibodies, such as anti-human antibodies, able to detect specific antibodies for said at least one redox form. Said assay is advantageously an ELISA assay allowing the simultaneous quantitation of specific antibodies for at least one redox form in a biological sample, in particular in a human serum and/or CSF obtained from a subject. Said solid support is preferably a well-plate, a chip, beads or strips.

In a particular embodiment of the invention, the in vitro method comprises the steps of:

coating the solid support with at least one redox form of HMGB1, preferably at a concentration from 0.5 to 5 ng/ml, diluted in a coating buffer, optionally comprising (i) a reducing agent, in particular dithiothreitol (DTT), preferably 0.5 mM DTT, when the redox form of HMGB1 is fully reduced HMGB1 or (ii) a reactive oxygen species (ROS), in particular hydrogen peroxide ($H_2O_2$), preferably 100 mM $H_2O_2$, when the redox form of HMGB1 is oxidized-HMGB1;

washing the solid support;

blocking unbound sites with a saturation buffer, preferably comprising from 2 to 5% Bovine Serum Albumin (BSA);

optionally, treating the biological sample by an acid solution to dissociate the immune complexes found in the sample, preferably a treatment with a Glycine solution at a low pH;

adding the biological sample, preferably diluted from 1/800 to 1/2000, more preferably at 1/1000, to said solid support;

optionally, adding a secondary antibody having binding capacity for the quantitated antibodies in complex with a redox form of HMGB1, preferably diluted at 1/500;

quantitating the specific antibodies for at least one redox form of HMGB1.

Secondary antibodies having binding capacity for the quantitated antibodies in complex with a redox form of HMGB1 according to the invention may be an antibody conjugated to an enzyme, for example alkaline phosphatase-conjugated antibody, or an antibody conjugated to a fluorescence moiety that is well-known to the person skilled in the art. The dilution of the secondary antibodies has to be optimized for each batch of antibodies following protocols well-known to the person skilled in the art.

Another aspect of the invention concerns a kit that may be used to quantitate specific antibodies for at least one redox form of HMGB1 in a biological sample obtained from a subject, or to assess the state of progression of a disease or a disorder in which HMGB1 is involved, or to identify predisposition or diagnostic biomarkers of a disease or a disorder in which HMGB1 is involved, or to identify prognostic biomarkers of the state of progression of a disease or a disorder in which HMGB1 is involved, in a biological sample obtained from a subject who is known to suffer from said disease or disorder.

This kit comprises at least one redox form of HMGB1 protein, in particular of mammalian origin, preferably of human origin, or a HMGB1 derivative as long as this derivative binds to specific antibodies for at least one redox form as defined above, and optionally an acid dissociation solution which has a pH between 1 and 3, to dissociate HMGB1/anti-HMGB1 antibody complexes found in the biological sample when taken from the subject, without altering the binding ability of the anti-HMGB1 antibody, such as defined above, a reducing agent such as dithiothreitol (DTT), β-mercaptoethanol, TCEP (tris(2-carboxyl)phosphine), in particular dithiothreitol (DTT), and a reactive oxygen species (ROS) such as hydroxyl radical (.OH), hydrogen peroxide ($H_2O_2$), superoxide radical ($O_2^-$), oxygen ($O_2$) and singlet oxygen ($^1O_2$), in particular hydrogen peroxide ($H_2O_2$). Optionally, this kit may also contain a neutralization buffer, for example as defined above and/or secondary antibodies having binding capacity for the quantitated antibodies in complex with a redox form of HMGB1. Optionally, this kit may also contain a calibration reagent and/or directions for use, in particular a leaflet.

In a particular embodiment of the invention, the kit comprises at least one redox form of HMGB1 protein or derivatives thereof, an acid dissociation solution to dissociate HMGB1/anti-HMGB1 antibody complexes, a reducing agent, preferably DTT, and ROS, preferably $H_2O_2$.

The kit is implemented to quantitate specific antibodies for at least one redox form of HMGB1 from any biological sample, in particular from blood, plasma, serum, saliva, peripheral blood mononuclear cells (PBMCs) or PBMC supernatant, CerebroSpinal Fluid (CSF) or other body fluids or tissues, preferably from serum and/or CSF, more preferably from human serum and/or CSF.

The invention is also directed to an in vitro method for assessing the state of progression of a disease or a disorder in which HMGB1 is involved, comprising quantitating specific antibodies for at least one redox form of HMGB1 according to the method of quantitating defined herein, in a biological sample obtained from a subject who is known to suffer from said disease or disorder;
wherein said biological sample is obtained from the same subject at different times relevant to assess the state of progression of said disease or disorder and wherein the increase over time of the level of specific antibodies for said at least one redox form of HMGB1 reflects the state of progression of said disease or disorder.

By "a subject who is known to suffer from a disease or disorder in which HMGB1 is involved", it is meant a subject or patient who has been positively and accurately diagnosed for a disease or disorder in which HMGB1 is involved, and for whom said disease or disorder has been confirmed following relevant testing.

The expression "assessing the state of progression of a disease or a disorder in which HMGB1 is involved" refers to the identification of the various stages met in the progression of said disease or disorder, for example an earlier or an advanced stage of said disease or disorder. When applied to a HIV-infected patient with neurological disorders, it refers to the neurological disorders stages (1 to 4) classification proposed as described below. Alternatively, the classification proposed by Antinori et al. as described below and referring to no HAND (HIV-associated neurological disorders) and HAND patients may also be considered.

The invention is also directed to an in vitro method for the identification of predisposition (or risk) or diagnostic biomarkers of a disease or a disorder in which HMGB1 is involved, comprising:
a) in biological samples obtained from subjects known to suffer from said disease or disorder, individually quantitating specific antibodies for each of fully reduced HMGB1, disulfide-HMGB1 and oxidized-HMGB1 by carrying out a method of quantitating defined herein;
b) comparing the level of specific antibodies for each of fully reduced HMGB1, disulfide-HMGB1 and oxidized-HMGB1 in said biological samples with the level of specific antibodies for each of fully reduced HMGB1, disulfide-HMGB1 and oxidized-HMGB1 determined from healthy donors; wherein specific antibodies for one of the redox form of HMGB1 selected from the group of said fully reduced HMGB1, disulfide-HMGB1 and oxidized-HMGB1 are qualified as predisposition (or risk) or diagnostic biomarkers when their level vary, in particular increase, between subjects suffering from said disease or disorder and healthy donors.

The terms "predisposition" or "predisposing" refer to the possibility to evaluate, at the time the quantitation of the specific antibodies for at least one redox form of HMGB1 is carried out on a sample obtained from a subject, the risk for the subject to develop or to progress toward a disease or a disorder in which HMGB1 is involved.

The term "diagnostic" refers to the possibility to determine for a subject, at the time the quantitation of the specific antibodies for at least one redox form of HMGB1 is carried out on a sample obtained from this subject, the presence or the absence of a disease or a disorder in which HMGB1 is involved.

The identification of predisposition or diagnostic biomarkers of a disease or a disorder in which HMGB1 is involved according to the invention constitutes a complementary indicator to qualify the predisposition (risk) or the diagnosis of said disease or disorder previously suspected, envisioned or obtained using conventional clinical methods.

The term "healthy donors" refers to adults (men or women) in good health, meaning that no disease or infection has been detected in the donor at the time the biological sample is taken from said donor, similarly to criteria used for blood donors. A donor according to the invention may refer to a single individual or a group of individuals or a pool of individuals.

The expression "the level of specific antibodies for at least one redox form of HMGB1" refers to the quantity of specific antibodies for at least one redox form of HMGB1. It may also refer to the difference between the quantity of specific antibodies for at least one redox form of HMGB1 in a biological sample obtained from a subject known to suffer from a disease or disorder in which HMGB1 is involved and a pre-determined quantity of specific antibodies for at least one redox form of HMGB1. Said pre-determined quantity of said antibodies corresponds to a reference value that may be defined as the mean value or the median value of the quantity of said antibodies in samples obtained from different healthy donors, i.e. from different individuals, or as the value of the quantity of said antibodies in a sample from the same subject at a different time, or as the mean value or the median value of the quantity of said antibodies in samples obtained from groups of subjects.

The invention is also directed to an in vitro method for the identification of prognostic biomarkers of the state of progression of a disease or a disorder in which HMGB1 is involved, in a biological sample obtained from a subject who is known to suffer from said disease or disorder, comprising:

a) in biological samples obtained from the same subject at different times, individually quantitating specific antibodies for fully reduced HMGB1, disulfide-HMGB1 and oxidized-HMGB1 by carrying out the method of quantitating as defined herein;

b) comparing the level of specific antibodies for each of fully reduced HMGB1, disulfide-HMGB1 and oxidized-HMGB1 in said biological samples;

wherein specific antibodies for one of the redox form of HMGB1 selected from the group of said fully reduced HMGB1, disulfide-HMGB1 and oxidized-HMGB1 are qualified as prognostic biomarkers of the state of progression of said disease or disorder when their level vary, in particular increase, over time.

The term "prognostic" refers to the possibility to evaluate, at the time the quantitation of the specific antibodies for at least one redox form of HMGB1 is carried out on a sample obtained from a subject, the risk for the subject to progress toward a more severe stage of an already diagnosed disease or disorder in which HMGB1 is involved.

The in vitro method for assessing the state of progression of a disease or a disorder in which HMGB1 is involved, or the identification of predisposition, prognostic or diagnostic biomarkers of a disease or a disorder in which HMGB1 is involved according to the invention are applicable to diseases or disorders in which HMGB1 is shown to be involved and associated with a pathological risk or condition. Said disease or disorder can be a chronic inflammatory disease and/or an infectious disease, e.g. bacterial infection, pathogen infection, viral infection or infection by prion.

In a particular embodiment, said disease or disorder in which HMGB1is involved is human immunodeficiency virus (HIV) infection, preferably an HIV infection associated with neurological disorders or HIV-associated neurocognitive disorders (HAND).

In another particular embodiment, when said disease is an infection (by a pathogen, bacteria or virus), preferably HIV infection, more preferably HIV-associated neurocognitive disorders (HAND), the biological sample is obtained either during primary or acute infection or during chronic infection.

The expression "HIV infection associated with neurological disorders" or "HIV-associated neurocognitive disorders (HAND)" encompasses neurological disorders of the nervous system which are caused directly by the HIV virus, by certain cancers and/or opportunistic infections, as well as disorders of unknown origin which are influenced by but are not known to be caused directly by the virus. Some of these neurological disorders associated with HIV may be characteristic of the state of progression of the disease, as defined above. Examples of neurological disorders associated with HIV are AIDS dementia complex (ADC) or HIV-associated encephalopathy, central nervous system lymphomas, cryptococcal meningitis, cytomegalovirus (CMV) encephalitis, encephalitis and myelitis caused by the herpes zoster virus, neuropathy (peripheral neuropathy and distal sensory polyneuropathy), neurosyphilis, progressive multifocal leukoencephalopathy (PML), toxoplasma encephalitis or cerebral toxoplasmosis and vacuolar myelopathy.

HIV-infected patients may be classified according to several parameters such as viral load, CD4 T cells number or clinical symptoms of AIDS.

In patients suffering from neurological disorders, a particular classification is based on these neurological disorders associated with HIV infection, as determined by clinicians, as follows;

Stage 1, with normal NP (Neuropsychological) testing;

Stage 2, with at least 2 SD (standard deviation) below the mean in one cognitive test or at least 1 SD below the mean in more than 1 test exploring the same domain. These results define the condition of ND (neuropsychological deficit);

Stage 3, including patients with criteria for ANI (Asymptomatic Neurocognitive Impairment); and Stage 4, including patients with MND and HAD (Mild Neurological Disorders and HIV-Associated Dementia).

This classification may be linked to the classification proposed by Antinori et al. (Neurology. 2007 Oct. 30, 69(18): 1789-1799) as follows: patients with no HAND (HIV-associated neurological disorders) include stage 1 and stage 2, whereas patients with HAND include stage 3 and stage 4.

In a preferred embodiment of the invention, the above-mentioned in vitro methods of the invention comprise quantitating specific antibodies for oxidized-HMGB1. In a more preferred embodiment of the invention, specific antibodies for oxidized-HMGB1 are qualified as predisposition, prognostic or diagnostic biomarkers.

In another preferred embodiment of the invention, the above-mentioned in vitro methods of the invention comprise quantitating specific antibodies for oxidized-HMGB1 and/or specific antibodies for disulfide-HMGB1 and the disease is human immunodeficiency virus (HIV) infection. More preferably, the above-mentioned in vitro methods of the invention comprise quantitating specific antibodies for oxidized-HMGB1 and the disease is HIV-associated neurocognitive disorders (HAND).

In another preferred embodiment of the invention, the above-mentioned in vitro methods of the invention comprise quantitating specific antibodies for at least one redox form of HMGB1, wherein said at least one redox form of HMGB1 is selected from the group of fully reduced HMGB1, disulfide-HMGB1 and oxidized-HMGB1, and wherein the disease is human immunodeficiency virus (HIV) infection and wherein the subject who is known to suffer from said disease is a subject with no HIV-associated neurocognitive disorders (HAND). Subjects with no HAND include stage 1 and stage 2 as previously defined, and reported by Antinori et al. (Neurology. 2007 Oct. 30, 69(18): 1789-1799).

In another preferred embodiment of the invention, said disease or disorder in which HMGB1 is involved is human immunodeficiency virus (HIV) infection, preferably an HIV infection associated with neurological disorders or HIV-associated neurocognitive disorders (HAND) and the specific antibodies for oxidized-HMGB1 and/or the specific antibodies for disulfide-HMGB1 and/or the specific antibodies for fully reduced HMGB1 are qualified as predisposition, prognosis or diagnostic biomarkers.

Another aspect of the invention concerns an in vitro method for screening targets for at least one redox form of HMGB1 comprising the steps of:

contacting a determined compound with at least one distinct redox form of HMGB1 or HMGB1 derivatives as long as these derivatives bind to specific antibodies for at least one redox form of HMGB1 as defined above; and detecting interaction, especially binding, of said compound with one or more of said specific redox forms of HMGB1 or HMGB1 derivatives as long as these derivatives bind to specific antibodies for at least one redox form of HMGB1, wherein the redox form of HMGB1 is selected from the group of fully reduced HMGB1, disulfide-HMGB1 and oxidized-HMGB1.

BRIEF DESCRIPTION OF THE DRAWINGS

FIG. 1. Redox state of HMGB1 and functions.

FIG. 2. Principle of the assay.

EXAMPLES

Figure 3A:
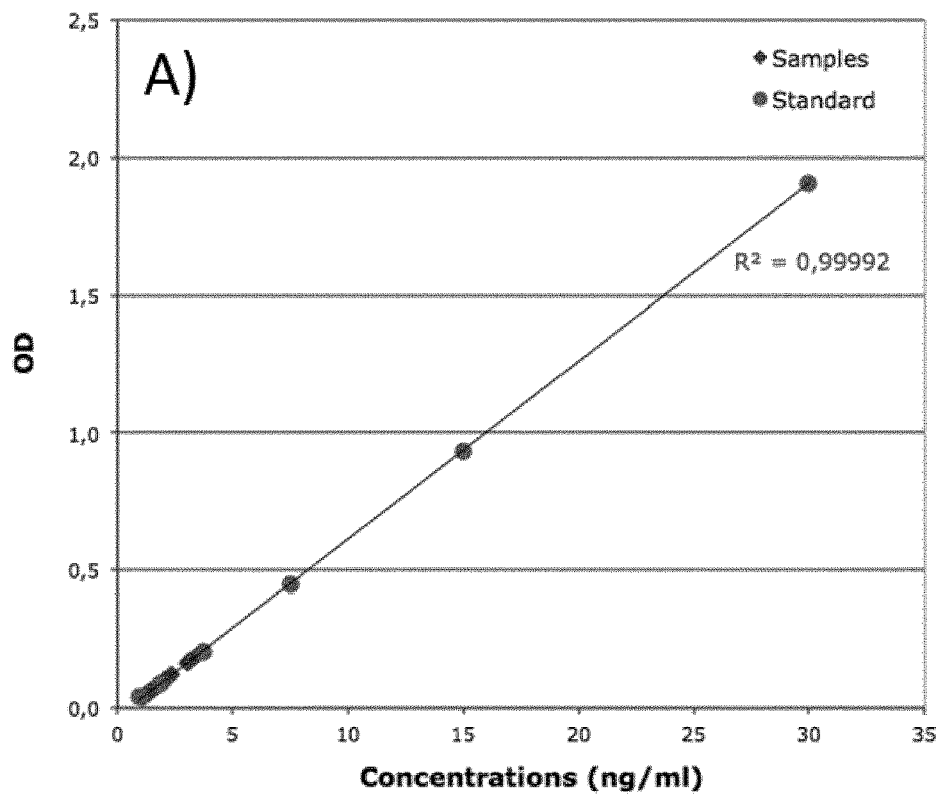
FIGS. 3A, 3B and 3C. Interference in the assay. The plate was coated with 3 µg/ml non-oxidizable HMGB1 in Dulbecco's Phosphate-Buffered Saline (DPBS) and HMGB1-specific antibodies concentrations were determined on serial dilutions (from 1/45 to 1/210) of a serum from a healthy donor (HD).

I. ELISA Assay for the Detection and Quantification of Human Specific Antibodies for Oxidized HMGB1, Disulfide HMGB1, Fully Reduced HMGB1, Non-Oxidizable Chemokine HMGB1 and HMGB1 Box B The assay was developed in two steps:

1. Initially, the inventors optimized the experimental conditions coating the ELISA plates with the non-oxidizable HMGB1 form.

2. Thereafter, the inventors tested the ability of the assay to detect the presence in human serum of anti-HMGB1 specific antibodies for different redox forms of HMGB1 protein.

The following reagents were used:

Disulfide HMGB1 (HMGBiotech, HM-122). Structurally, Disulfide HMGB1 has a disulfide bridge between cysteine residues 23 and 45 and a reduced cysteine residue 106. The Disulfide HMGB1 is the natural protein.

Fully reduced HMGB1 (HMGBiotech, HM-116) produced in E. coli. This formulation is fully reduced, it is the natural protein.

Non-oxidizable chemokine-HMGB1 (HMGBiotech, HM-132), produced in E. coli, it is a mutant protein where all cysteines are replaced with serines, it is resistant to inactivation by ROS.

Recombinant Box B from HMGB1 (HMGBiotech, HM-052), corresponding to the amino acids 89 to 163 of HMGB1, produced in E. coli from an expression plasmid coding for the mammalian sequence, which is totally identical in human and mouse.

Anti-HMGB1 monoclonal antibody DPH1.1 (HMGBiotech, HM-901).

Mouse anti-HMGB1 antibody 1E6-E10 (Serotec, Ref MCA4045Z).

Human IgG from serum (Sigma; reference I2511) are used as standards during ELISA for IgG antibodies detection.

Anti-human IgG (Fc specific)-alkaline phosphatase antibody produced in goat (Sigma; Ref A9544).

SIGMAFAST™ p-Nitrophenyl phosphate (pNPP substrate) Tablets (Sigma; reference N2770).

MicroWell flat-bottom 96-well plates Nunc (VWR international; reference 62409-112).

Antibodies which bind to HMGB1 are known and can be produced by methods well-known in the art. Examples of commercially available anti-HMGB1 antibodies are anti-HMGB1 monoclonal antibody DPH1.1 (HMGBiotech, HM-901) or 1E6-E10 antibody (Serotec, Ref MCA4045Z). These methods include those which produce polyclonal antibodies to HMGB1 and monoclonal antibodies to HMGB1 or to specific fragments of HMGB1. These antibodies are preferably derived from the same species as the subject to which they are administered and recognized or are induced to the HMGB1 of the same species to which they will be administered. These antibodies may have different isotypes, such as IgA, IgG or IgM isotypes. Antibody fragments which bind HMGB1 may also be employed, including Fab, $Fab_2$, and single chain antibodies or their fragments.

The ELISA assay to quantitate total specific antibodies for different redox forms of HMGB1 was carried out as follows:

Coating of 96-well plates was performed overnight at 4° C. with 3 µg/ml of the different redox forms of HMGB1 or Box B diluted in DPBS (Dulbecco's Phosphate-Buffered Saline). Simultaneously, coating of serial dilutions of human IgG in DPBS was performed to serve as standards. The different forms of HMGB1 used were: all-thiol, disulfide, oxidized (Ox) and the non-oxidizable (Non-Ox) mutant. In order to maintain (or obtain) the reduced state of the protein, DTT was added to the appropriate wells at a concentration of 1 mM. The oxidized form was obtained adding $H_2O_2$ (100 mM) to the disulfide HMGB1.

Plates were washed four times with DPBS/0.05% (v/v) TWEEN® 20 (washing buffer), using a microplate washer (Atlantis; Oasys). Similar washings were performed after each step of the ELISA assay. Unbound sites were blocked at 37° C. for 2 hours with DPBS/2% (w/v) BSA (saturation buffer).

Serum samples were treated with one volume of 1.5M Glycine (pH 1.85) for 30 min at 25° C. in a water bath, and further kept on ice and diluted with 1.5M Tris, v/v, pH 9.0. 100 µl aliquots of serum samples were then immediately diluted (from 1/3 to 1/6000) in DPBS/0.05% (v/v) TWEEN® 20/1% (w/v) BSA (antibody dilution buffer), distributed on coated plates and incubated for 1 hour 30 min at 37° C.

Goat anti-human IgG alkaline phosphatase-conjugated antibodies were diluted 1/500 in DPBS/0.05% (v/v) TWEEN® 20/1% (w/v) BSA and added for 1 hour at 37° C.

Detection of antigen-specific antibodies was performed after 30 min of incubation at 37° C. with 100 µl pNPP substrate. The reaction was stopped by addition of 100 µl NaOH 3M and the optical density was read with a Tecan plate reader at 405 nm. Concentration of HMGB1- or BOX B-specific antibodies was calculated according to the standard curve obtained from standard immunoglobulin solution absorbance (FIG. 2).

II. Calibration of the ELISA Assay

To develop this assay, different parameters were assessed using non-oxidizable HMGB1-coated plates:

(i) Assessment of the optimal BSA concentration to saturate wells coated with HMGB1: 2% to 5% BSA concentrations were equally efficient.

(ii) Assessment of the optimal anti-IgG-PAL antibody concentrations (secondary antibody) to reveal bound anti-HMGB1 antibodies: 1/500 dilution was chosen, giving the best results in terms of linearity for batch of antibodies in use.

(iii) Assessment of the optimal HMGB1 concentration in coating buffer: concentrations from 2.5 to 5 µg/ml were the most appropriate.

III. Screening for Interference in the Assay

Once these conditions optimized, the inventors tested the assay for interference and reproducibility.

Figure 3B:
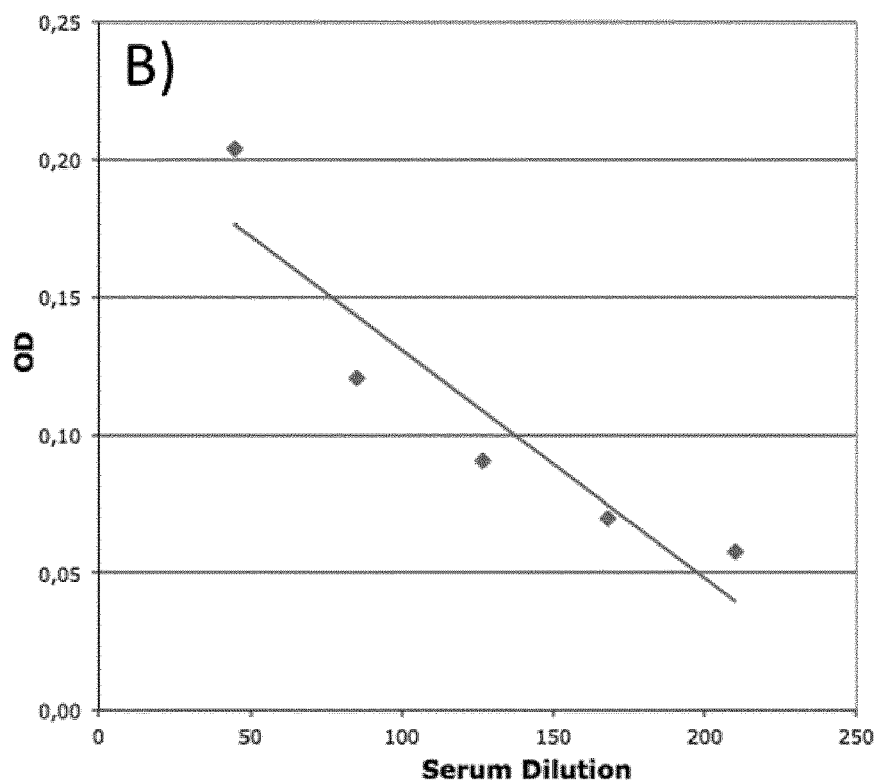
Figure 3C:
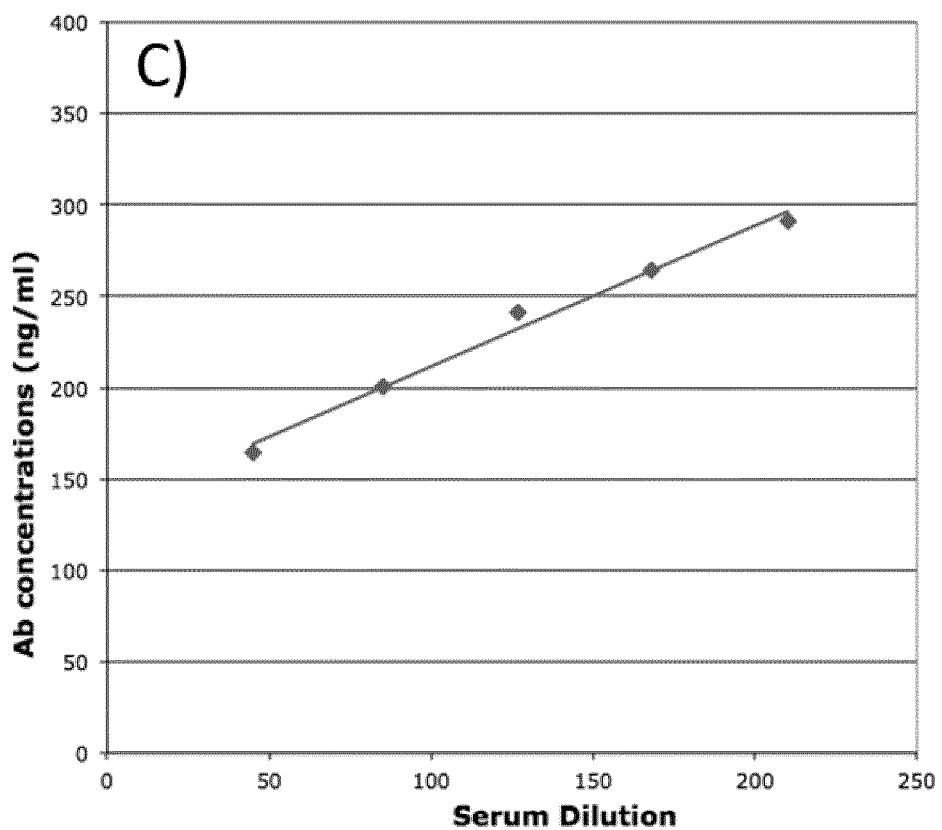

The standard curves with human IgG always showed a coefficient of determination >0.99 and the samples fell within the standard concentrations (FIG. 3A). As expected, an inverse correlation between sample dilutions and optical density (OD) was observed (FIG. 3B). Nevertheless, once the antibodies concentrations were extrapolated using the standard curve, the inventors noticed an interference effect in the assay (FIG. 3C). The inventors therefore tested different conditions to resolve this issue: adding deoxycholate or TWEEN® 20 to the assay buffers and further diluting the samples.

Influence of Deoxycholic Acid on Interference

Figure 4:
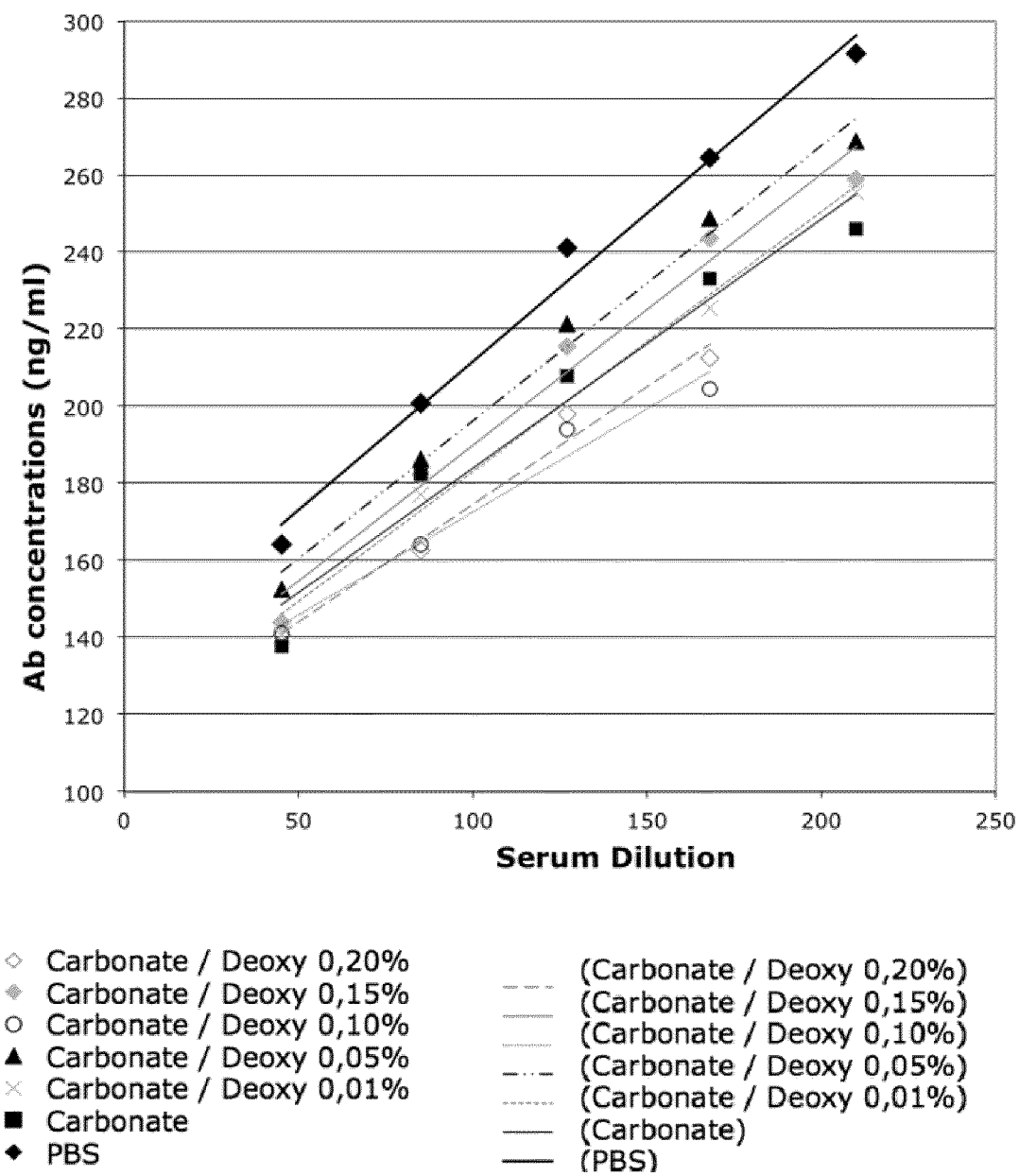
FIG. 4. Influence of deoxycholic acid concentrations on interference. The plate was coated with 3 µg/mL non-oxidizable HMGB1 in
DPBS or carbonate-bicarbonate buffer containing different concentrations of deoxycholic acid. HMGB1-specific antibodies concentrations were determined on serial dilutions (from 1/50 to 1/210) of a HD serum.

Adding deoxycholic acid to the coating buffer did not solve the interference problem of the assay, as shown in FIG. 4.

Effect of TWEEN® 20 on Interference

Figure 5:
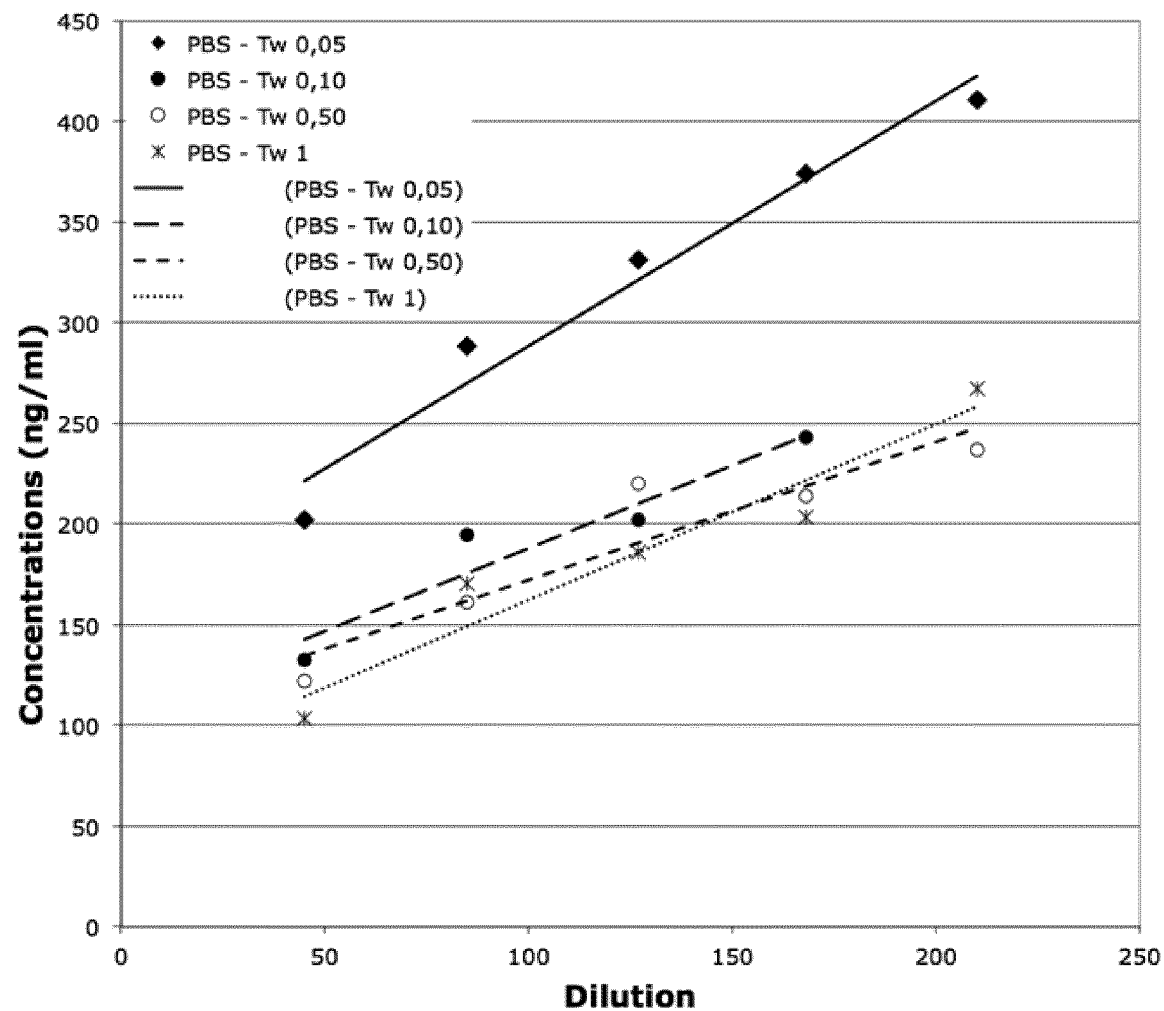
FIG. 5. Effect of TWEEN® 20 on interference. Plates were coated with 3 µg/ml non-oxidizable HMGB1 in DPBS. Increasing concentrations of TWEEN® 20 were added to the washing buffer and the antibody dilution buffer. HMGB1-specific antibodies concentrations were determined on serial dilutions (from 1/50 to 1/210) of a HD serum.

Adding TWEEN® 20 to the washing buffer and to the antibody dilution buffer did not influence the interference problem of the assay (FIG. 5).

Effect of Serum Dilution on Interference

Figure 6:
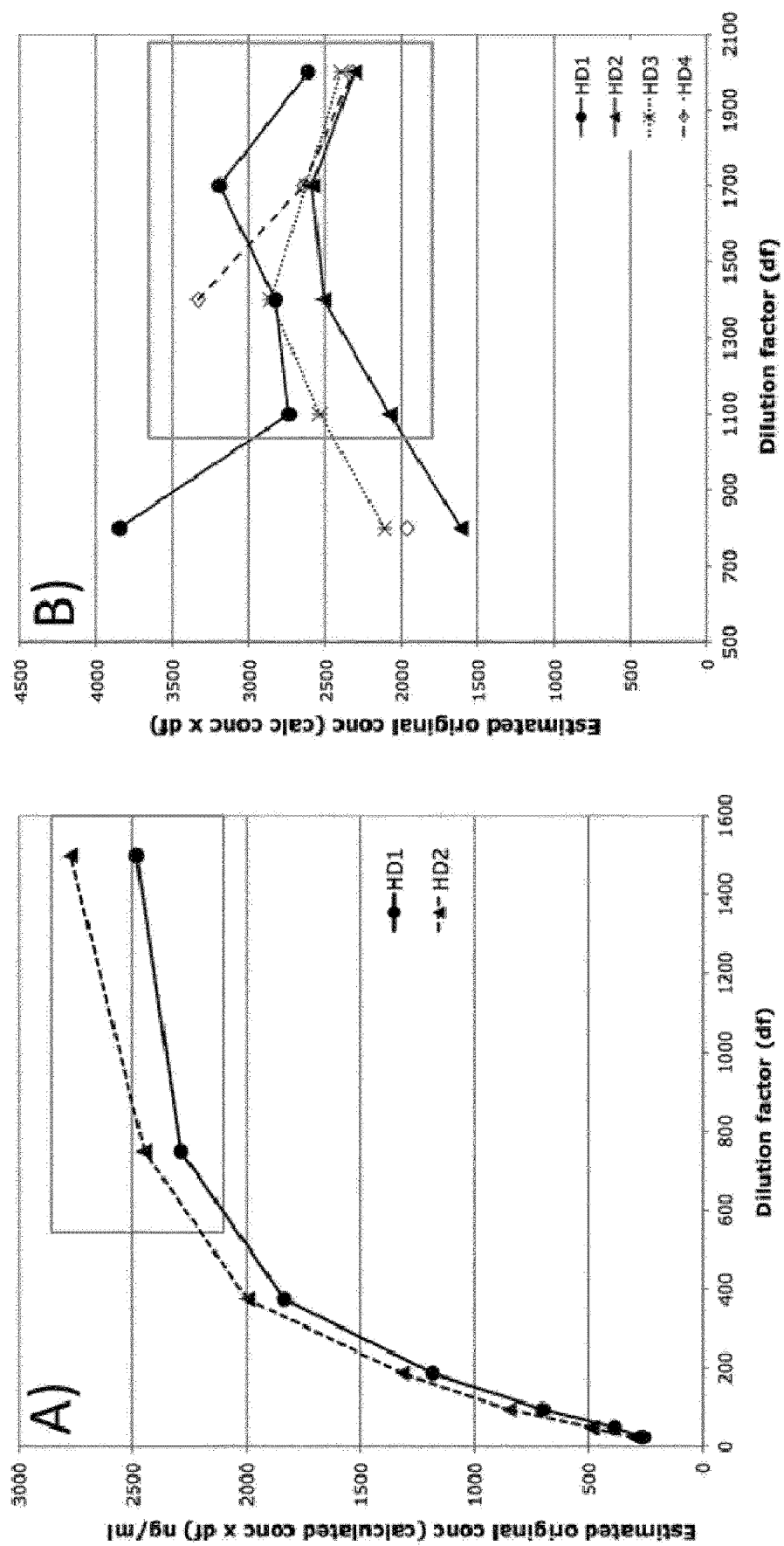
FIG. 6. Effect of serum dilution on interference. Plates were coated with 3 µg/ml non-oxidizable HMGB1 in DPBS. HMGB1-specific antibodies concentrations were determined on serial dilutions of different HD sera, from 1/3 to 1/6000 (A) or from 1/800 to 1/2000 (B).

Serial dilutions of the serum revealed a decrease in interference for dilutions over 1/800. Serum dilutions 1/3000 resulted into no antibody detection (FIG. 6).

IV. Acidic Treatment for the Detection of Total Anti-HMGB1 Antibodies in Human Samples To determine the assay conditions required for testing human biological samples, a series of human sera have been titrated for the presence of HMGB1-specific antibodies, and assuming that [HMGB1-anti-HMGB1 antibody] complexes were present in biological samples, the influence of pre-treatment with Glycine 1.5M, pH 1.85 to dissociate these immune complexes has been assessed. Serum samples have been either untreated or treated with 1.5M Glycine (v/v, pH 1.85) for 30 min at 25° C. in a water bath, and further kept on ice and diluted with 1.5M Tris, v/v, pH 9.0. Samples were then immediately diluted and distributed on coated plates and tested as described above.

Figures 7, 8A:
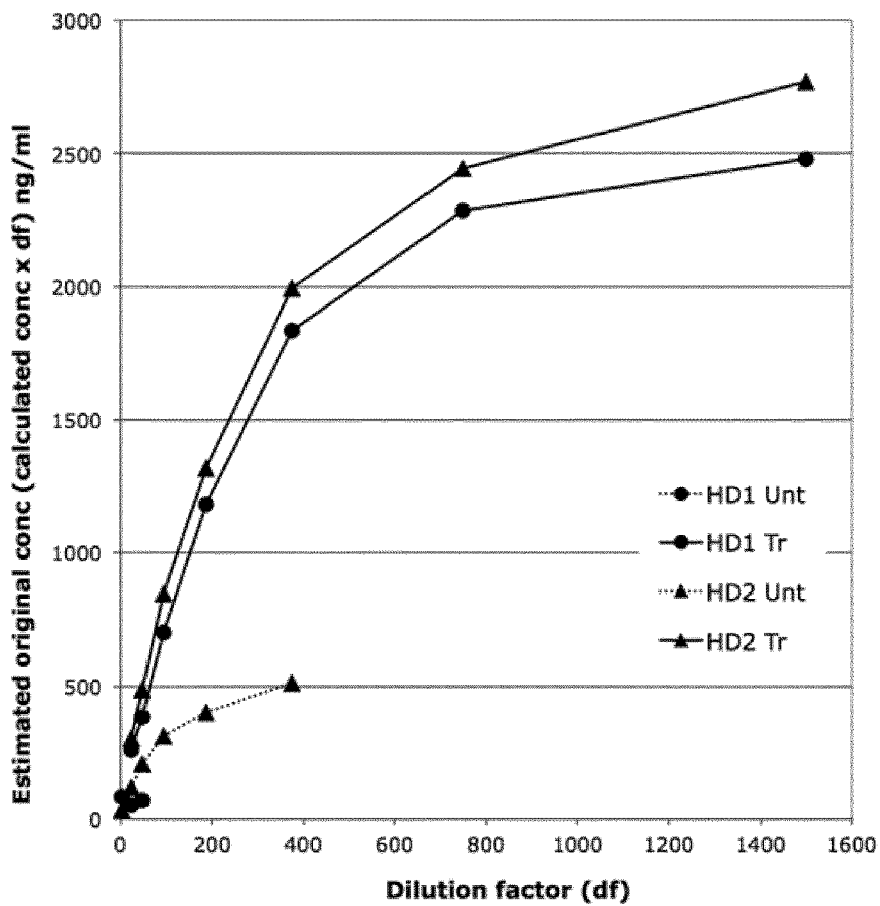
FIG. 7. Acidic treatment for the detection of total anti-HMGB1 antibodies in human samples. Human sera, either untreated (Unt) or treated (Tr) with Glycine 1.5M, were titrated for the presence of anti-HMGB1 IgG antibodies. Circulating residual anti-HMGB1 antibodies were detected at very low levels, while total anti-HMGB1 antibodies, including the complexed ones were detected at high levels following the acidic treatment. The plates were coated with 3 µg/ml non-oxidizable HMGB1 in DPBS.
FIGS. 8A and 8B. Reproducibility. The serum from one HD was used as internal control in different experiments to test the reproducibility of the assay. The plates were coated with 3 µg/ml non-oxidizable HMGB1 in DPBS.

Data in FIG. 7 show that total anti-HMGB1 antibodies were barely detected in human sera, unless they were pretreated with Glycine 1.5M to dissociate the immune complexes.

V. Reproducibility

Figure 8B:
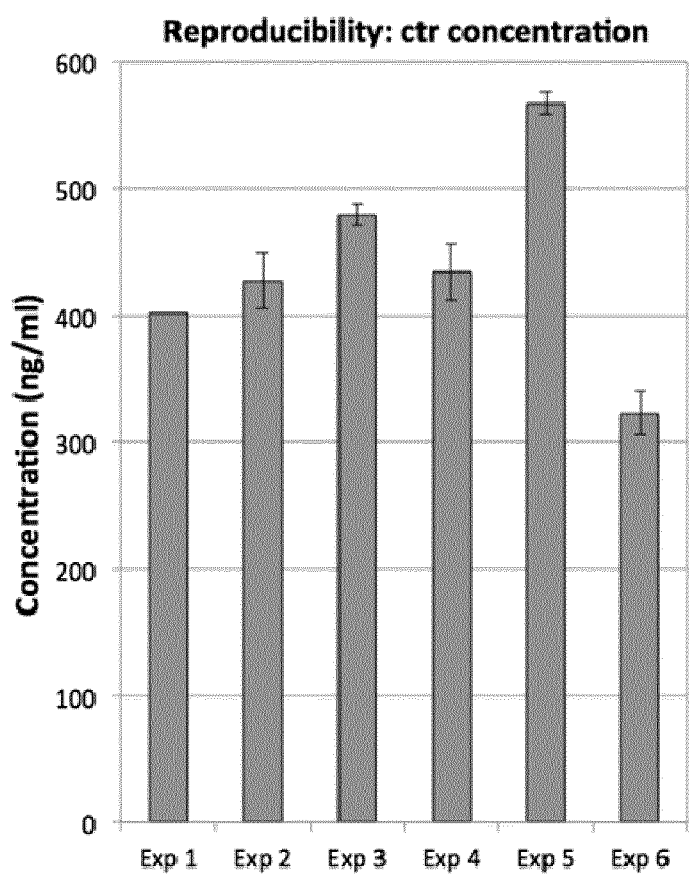

The mean coefficient of variation of replicate samples within a plate was 3.8% (FIG. 8A), and the coefficient of variation of the results obtained testing the same serum in 6 different experiments was 18.5% (FIGS. 8A and 8B).

VI. Effect of DTT on Monoclonal Antibodies Binding:

Depending on its redox state, HMGB1 exhibits different functions. All-thiol HMGB1 can be maintained in the presence of DTT, while the disulfide form can be induced by $H_2O_2$ treatment. Prolonged exposition to $H_2O_2$ leads to the oxidized form (FIG. 1).

Figure 9:
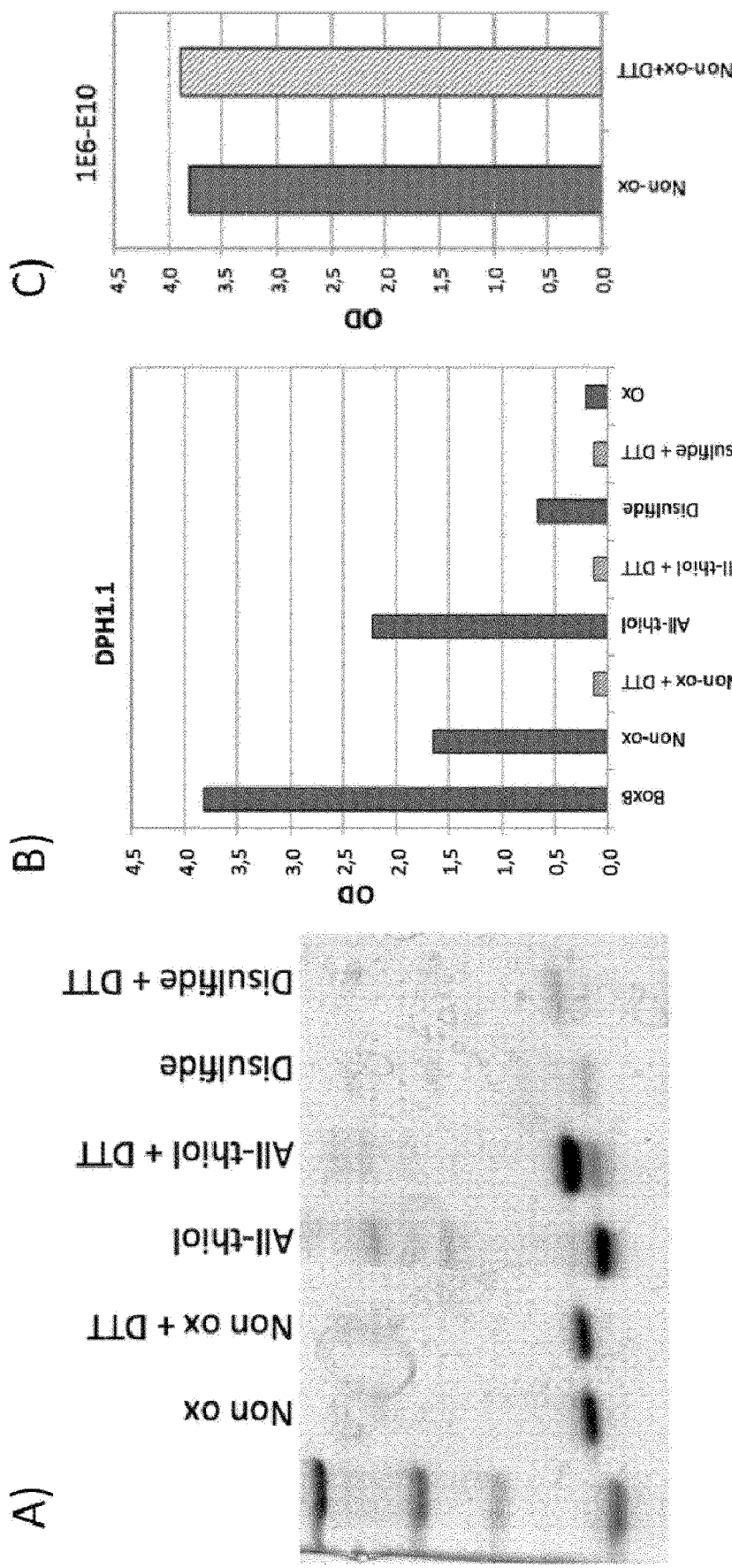
FIG. 9. Impact of DTT on the specific detection of various redox forms of HMGB1. Different forms of HMGB1 were run on a 12% polyacrylamide gel in the presence or the absence of 1 mM DTT (A). Plates were coated with 3 µg/ml of the different redox forms of HMGB1, as provided by HMGBiotech. In order to keep the reduced form of HMGB1, 1 mM DTT was added to the coating, saturation and antibody dilution buffers (B) or only during coating and saturation steps (C). 100 mM $H_2O_2$ was added to the coating buffer in order to obtain the oxidized form of HMGB1. The specificity of two different murine anti-HMGB1 monoclonal antibodies was tested: DPH1.1 (B) and 1E6-E10 (C).

The gel in FIG. 9A showed the impact of DTT (1 mM) on the different forms of HMGB1: as expected, non-oxidizable HMGB1 was insensitive to DTT, which did not induce any change in the MW, while the all-thiol molecule (chemokine) required DTT to be stabilized in the right form. Disulfide HMGB1 (cytokine) showed a lower MW compared to All-thiol molecule, as expected, which was increased in the presence of DTT, leading to the MW of All-thiol HMGB1. These data revealed the instability of the various forms of HMGB1, unless an appropriate DTT treatment is applied.

In order to validate the assay, the inventors tested the reactivity of two commercialized monoclonal antibodies (DPH1.1 and 1E6-E10) against the different forms of HMGB1. The plates were coated with various forms of HMGB1 (as obtained from HMGBiotech) and 1 mM DTT was added to specific wells to maintain the reduced state of the protein. FIG. 9B shows that DTT added to the antibody dilution buffer prevented antibody binding, while DTT added only during the coating and saturation steps did not affect the antibody binding (FIG. 9C).

VII. Ability of the Assay to Determine the Specificity of HMGB1-Specific Monoclonal Antibodies Towards the Various Redox Forms of HMGB1

Figure 10:
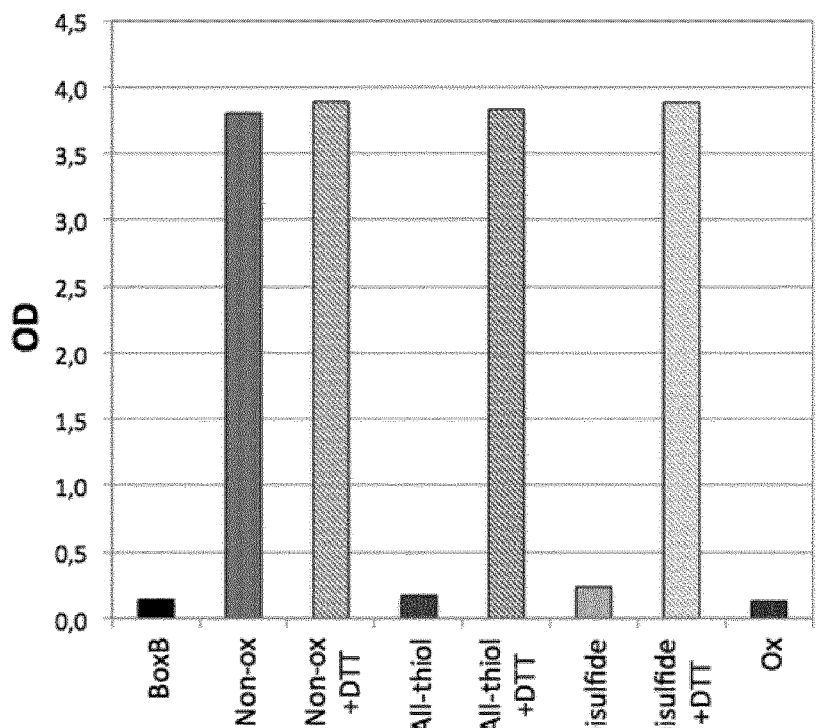
FIG. 10. Ability of the assay to determine the specificity of antibodies towards the various redox forms of HMGB1. Plates were coated with 3 µg/ml of the different redox forms of HMGB1, as provided by HMGBiotech. 1 mM DTT was added to the coating and saturation buffers in order to obtain the all-thiol form of HMGB1. 100 mM $H_2O_2$ was added to the coating buffer in order to obtain the oxidized form of HMGB1. The specificity of the mouse monoclonal antibody anti-HMGB1 1E6-E10 was tested on the different forms of the protein.

To assess the specificity of the assay, the inventors used the murine anti-HMGB1 antibody 1E6-E10, and first assessed to which form of HMGB1 it was directed. The inventors showed for the first time that 1E6-E10 binds to the non-oxidizable form (Non-ox form), in the presence or absence of DTT, but its binding to the all-thiol form was only detected in the presence of DTT (FIG. 10). This observation confirmed the instability of the reduced form of HMGB1 (as shown on the gel in FIG. 9A), which needs DTT to be stabilized in a reduced state. 1E6-E10 did not recognize the disulfide form, but it did recognize the disulfide form in the presence of DTT, which corresponded to the reduced form (as shown on the gel on FIG. 9A). It did not recognize the oxidized (ox) form either.

Altogether these data indicated that the assay allowed the determination of the specificity of HMGB1 antibodies towards various redox forms of HMGB1, provided they were kept in the right redox state.

Figure 11:
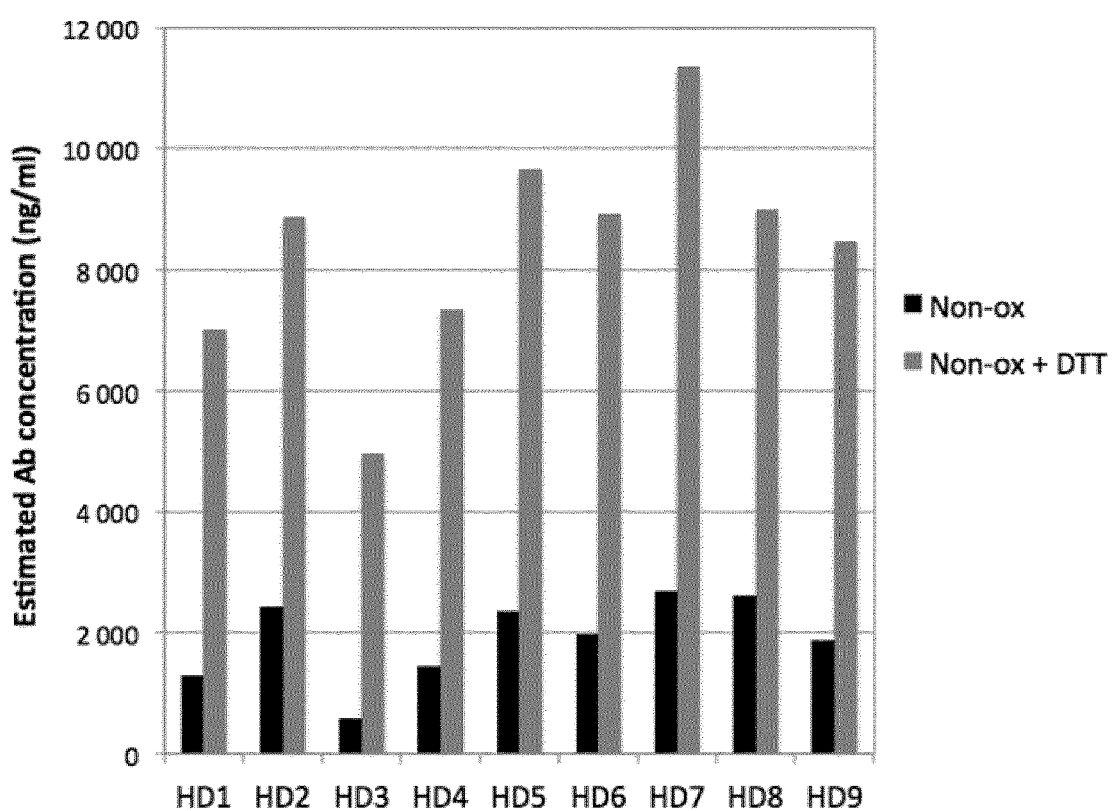
FIG. 11. Detection and quantification of antibodies to the mutant, non-oxidizable (Non-Ox) form of HMGB1, with or without DTT, in HD sera. Plates were coated with 3 µg/ml of the non-oxidizable form of HMGB1. 1 mM DTT was added to the coating and saturation buffers in order to verify the effect of DTT on the binding capacity of the antibodies. Titration of total antibodies recognizing the non-oxidizable form of HMGB1 was made in the serum of 9 HD (serum dilution 1/1500).

VIII. Effect of DTT on Detection of Anti-HMGB1 Antibodies in Healthy Donors (HD)' Sera Assuming that the mutant, non-oxidizable (Non-ox) form of HMGB1 was not subject to conformational changes following DTT-treatment, the quantification of specific antibodies for the Non-ox form of HMGB1 in human sera was carried out in the presence or absence of 1 mM DTT in both the coating and saturation buffers, in order to evaluate a possible effect of DTT on antibody binding. Indeed, DTT proved to have a very strong effect on the binding of the natural antibodies present in human serum (FIG. 11).

Figure 12:
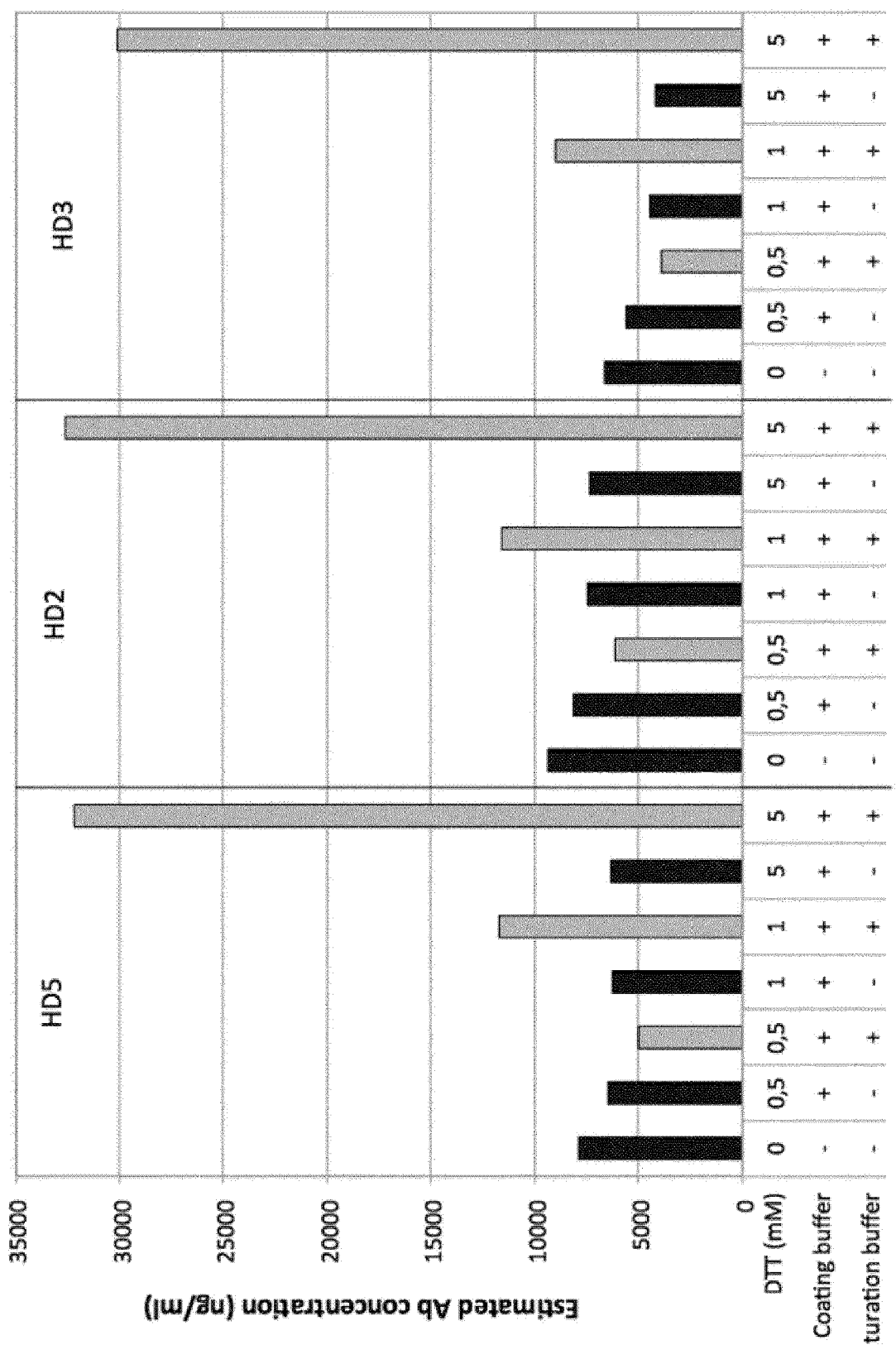
FIG. 12. Detection and quantification of antibodies to the mutant, non-oxidizable (Non-Ox) form of HMGB1, with different concentrations of DTT, in HD sera. Plates were coated with 3 µg/ml of the non-oxidizable form of HMGB1. 0.5 mM, 1 mM or 5 mM DTT was added to the coating and, for selected samples, to the saturation buffers in order to verify the effect of DTT on the antibodies binding capacity. Titration of total antibodies recognizing the non-oxidizable form of HMGB1 was made in the serum of 3 HD (serum dilution 1/1000).

The same experiment was therefore repeated using coating and saturation buffers containing different concentrations of DTT (0.5 mM, 1 mM and 5 mM) (FIG. 12). The amount of natural anti-HMGB1 antibodies present in 3 HD sera was estimated in different experimental conditions. The plate was coated with the non-oxidizable HMGB1 mutant in the presence of different concentrations of DTT. In selected samples, DTT was added at the same concentrations in the saturation buffer. HD samples were tested at a 1/1000 dilution. The presence of DTT in the saturation buffer had a strong effect on the antibody binding. Adding DTT at different concentration just to the coating buffer had a smaller impact on the assay results.

Given the results obtained, the following conditions were chosen for subsequent experiments: 0.5 mM DTT in the coating buffer and no DTT in the saturation buffer.

Figure 13:
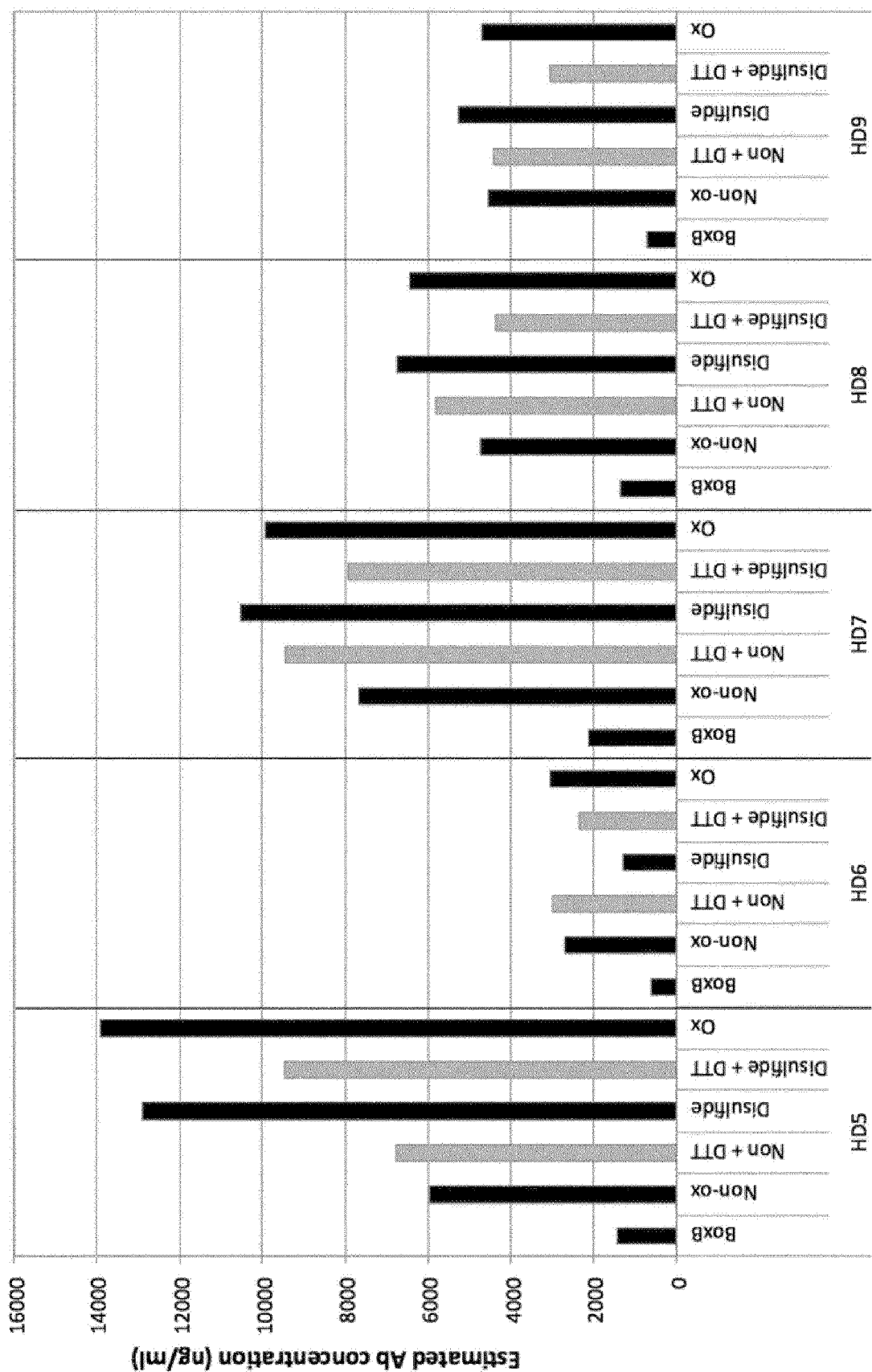
FIG. 13. Detection and quantification of antibodies to the different forms of HMGB1 in HD sera. Plates were coated with 3 µg/ml of the different forms of HMGB1. 0.5 mM DTT was added to the coating buffer in order to obtain the all-thiol form of HMGB1. 100 mM $H_2O_2$ was added to the coating buffer in order to obtain the oxidized form of HMGB1. Titration of total specific antibodies for the different forms of HMGB1 was made in the serum of 5 HD (serum dilution 1/1000).

IX. Detection and Quantification of Anti-HMGB1 Specific Antibodies for Different Redox Forms of HMGB1 and for the HMGB1 Segment Box B in Sera from Healthy Donors (HD) and HIV$^+$ Patients The assay was used to titrate serum anti-HMGB1 antibodies against the different forms of HMGB1 in sera from healthy donors (FIG. 13). These data showed for the first time that human sera from healthy donors contained specific antibodies for all redox forms of HMGB1: all-thiol, disulfide and oxidized. Human sera from healthy donors also contained specific antibodies for the protein segment Box B. Variable levels of these antibodies were detected in the five sera tested.

Figure 14:
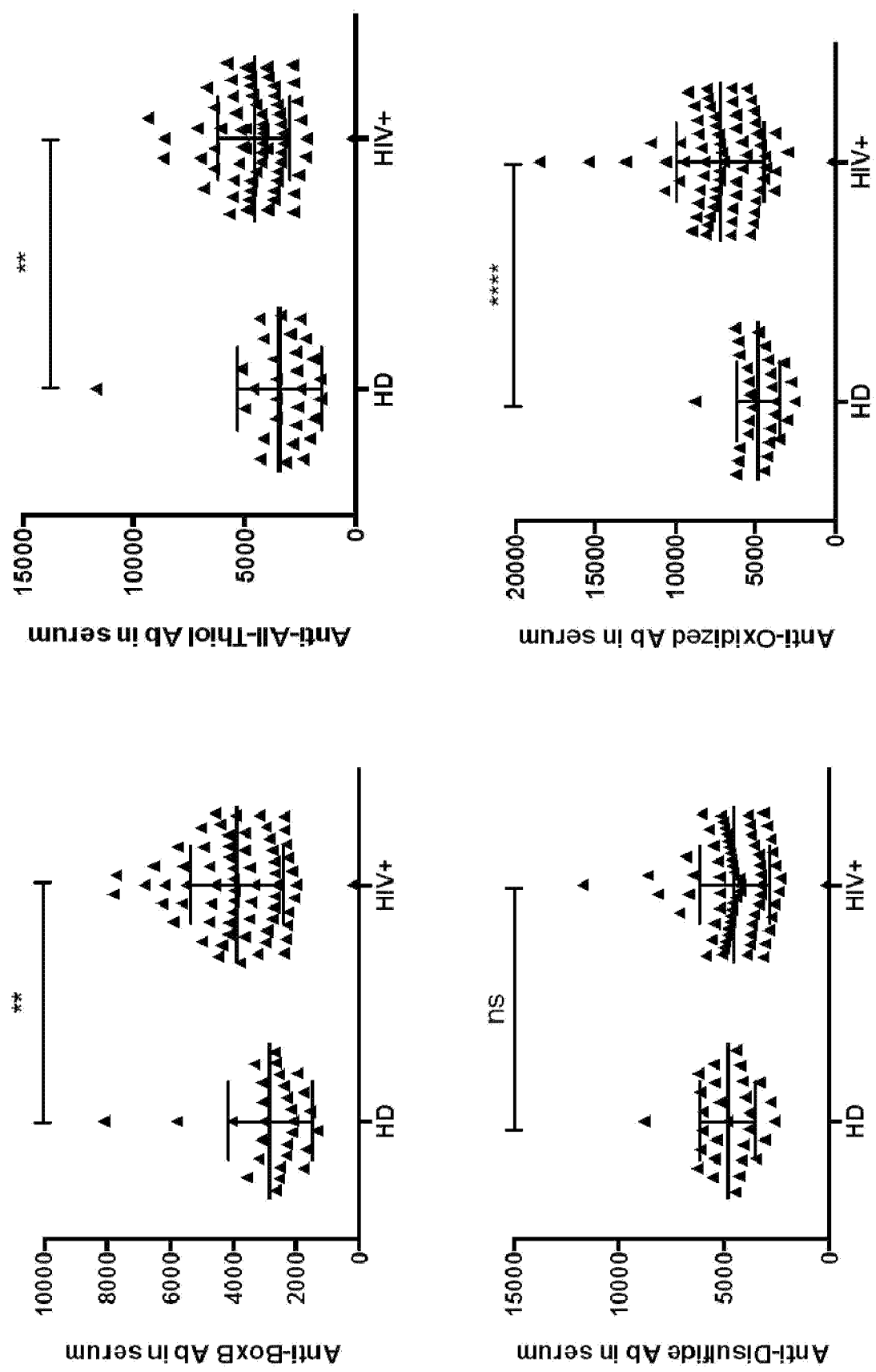
FIG. 14. Serum levels of specific antibodies for the different forms of HMGB1 in healthy donors (HD) and $HIV^+$ Patients. Plates were coated with 3 µg/ml of the different forms of HMGB1. 0.5 mM DTT was added to the coating buffer in order to obtain the all-thiol form of HMGB1. 100 mM $H_2O_2$ was added to the coating buffer in order to obtain the oxidized form of HMGB1. Titration of total specific antibodies for the different forms of HMGB1 was made in the serum of 29 HD and 68 HIV-infected patients (serum dilution 1/1000). Statistical significance for comparison of the 2 groups is shown: ns: not significant, $p<0.01$, **$p<0.0001$.6

Data in FIG. 14 confirm that sera from all healthy donors contained high levels of specific antibodies for the three redox forms tested and for the HMGB1 segment Box B. 29 healthy donors were tested, and mean concentrations of antibodies were the following:

Anti-Box B: mean 2834 ng/ml [mini 1378-maxi 8126]
Anti-all-thiol: mean 3447 ng/ml [mini 1636-maxi 11697]
Anti-disulfide: mean 3238 ng/ml [mini 1652-maxi 15603]
Anti-oxidized: mean 4825 ng/ml [mini 2596-maxi 8831]

The inventors then addressed the question of the levels of antibodies against the various redox forms of HMGB1 in the context of chronic HIV infection. The group of patients analyzed (n=68) was part of a cohort of 105 chronically HIV-infected patients, classified according to neurological disorders. Group 1 included HIV-1-infected patients without neurological disorders (stage 1: no HAND), whereas groups 2 (stage 2: no HAND with single deficit), 3 (stage 3: Asymptomatic Neurological Impairment—ANI) and 4 (stage 4: Mild Neurological Disorders and HIV-Associated Dementia—MND and HAD) included patients with increasing neurocognitive disorders. FIG. 14 shows that HIV-1 infection was associated with a statistically significant increase in the levels of specific antibodies for all-thiol and oxidized HMGB1. HIV-1 infection was also associated with a statistically significant increase in the levels of specific antibodies for Box B. In contrast, no difference was found in the levels of anti-disulfide antibodies when HIV patients were compared to healthy donors.

X. Quantification of Anti-HMGB1 Specific Antibodies for Different Redox Forms of HMGB1 and for the HMGB1 Segment Box B in Patients with HIV-Associated Neurological Disorders (HAND)

Figure 15:
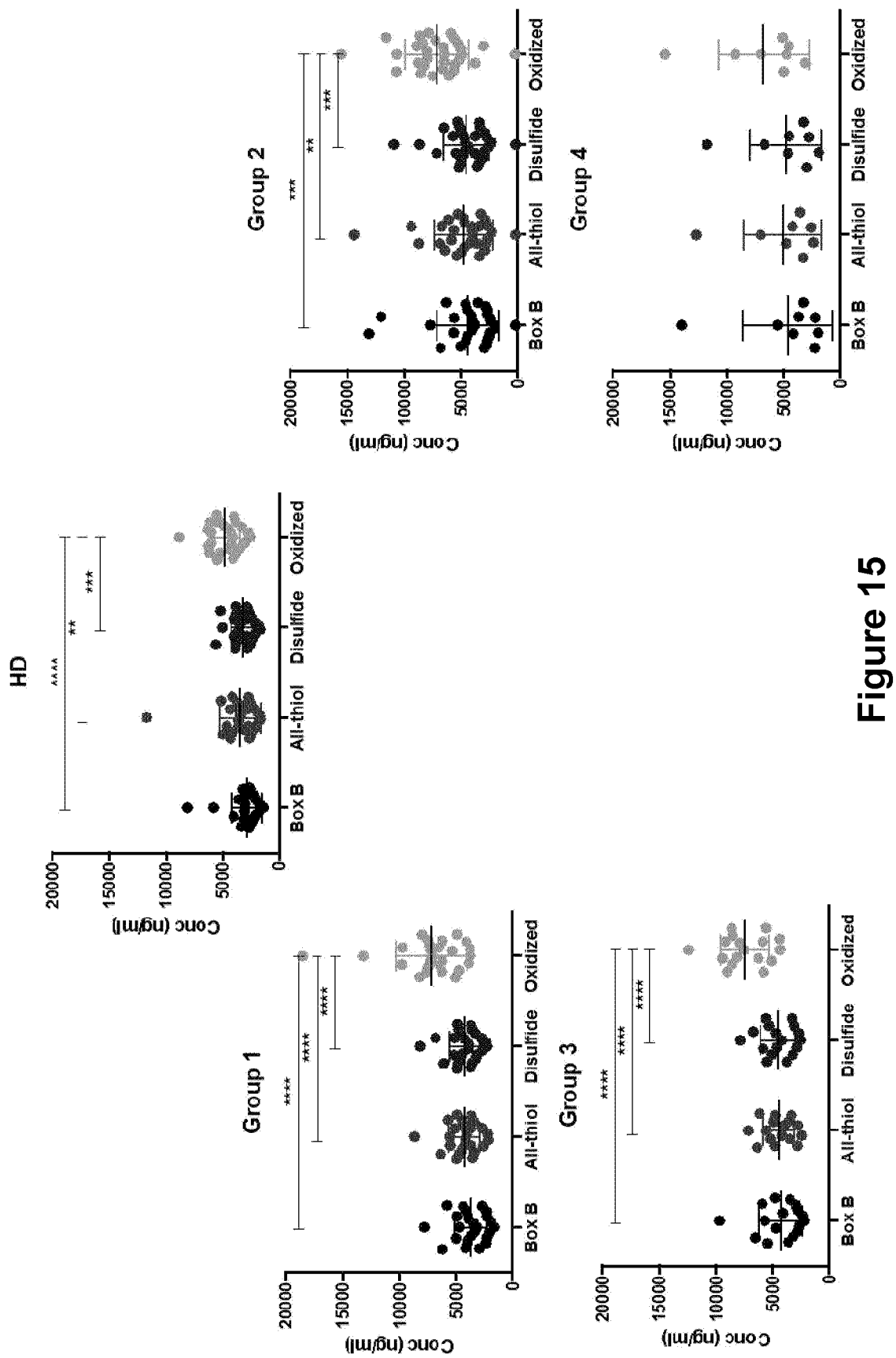
FIG. 15. Serum concentration of specific antibodies for the different forms of HMGB1 in patients with HIV-associated neurological disorders (HAND). Plates were coated with 3 µg/ml of the indicated forms of HMGB1. 0.5 mM DTT was added to the coating buffer in order to obtain the all-thiol form. 100 mM $H_2O_2$ was added to the coating buffer in order to obtain the oxidized form of HMGB1. Titration of total specific antibodies for the different forms of HMGB1 was made in the serum of 29 HD and 68 HIV-infected patients. Groups of patients were defined according to their clinical neurological status (group 1: stage 1, no HAND, n=22; group 2: stage 2, no HAND with single deficit, n=26; group 3: stage 3, ANI (Asymptomatic Neurological Impairment), n=12; group 4: stage 4, MND+HAD (Mild Neurological Disorders+HIV-Associated Dementia), n=8). Statistical significance is shown: $p<0.01$, *$p<0.001$, ****$p<0.0001$.

FIG. 15 shows the comparative levels of serum antibodies directed against the redox forms of HMGB1 and against the HMGB1 segment Box B in the patients classified in the 4 groups as described above according to their clinical neurological alterations. Strikingly, the levels of specific antibodies for the oxidized form were significantly increased as compared to the levels of specific antibodies for disulfide, all-thiol or Box B, and this was observed for all groups of subjects, including healthy donors. For group 4 (stage 4) a trend was observed but it did not reach statistical difference, probably due to the low number of subjects in this group.

XI. Specific Antibodies to Oxidized HMGB1 are a Biomarker of HIV Infection and HAND Concentrations of IgG antibodies (ng/ml) specific for the different redox forms of HMGB1 (all-thiol, disulfide, oxidized) and specific for Box B were determined in sera from healthy donors (HD) and HIV-1-infected patients grouped in stage/group 1 (no HAND), stage/group 2 (no HAND with single deficit), stage/group 3 (ANI—asymptomatic neurological impairment), and stage/group 4 (MND+HAD—Mild Neurological Disorders and HIV-Associated Dementia).

Figure 16:
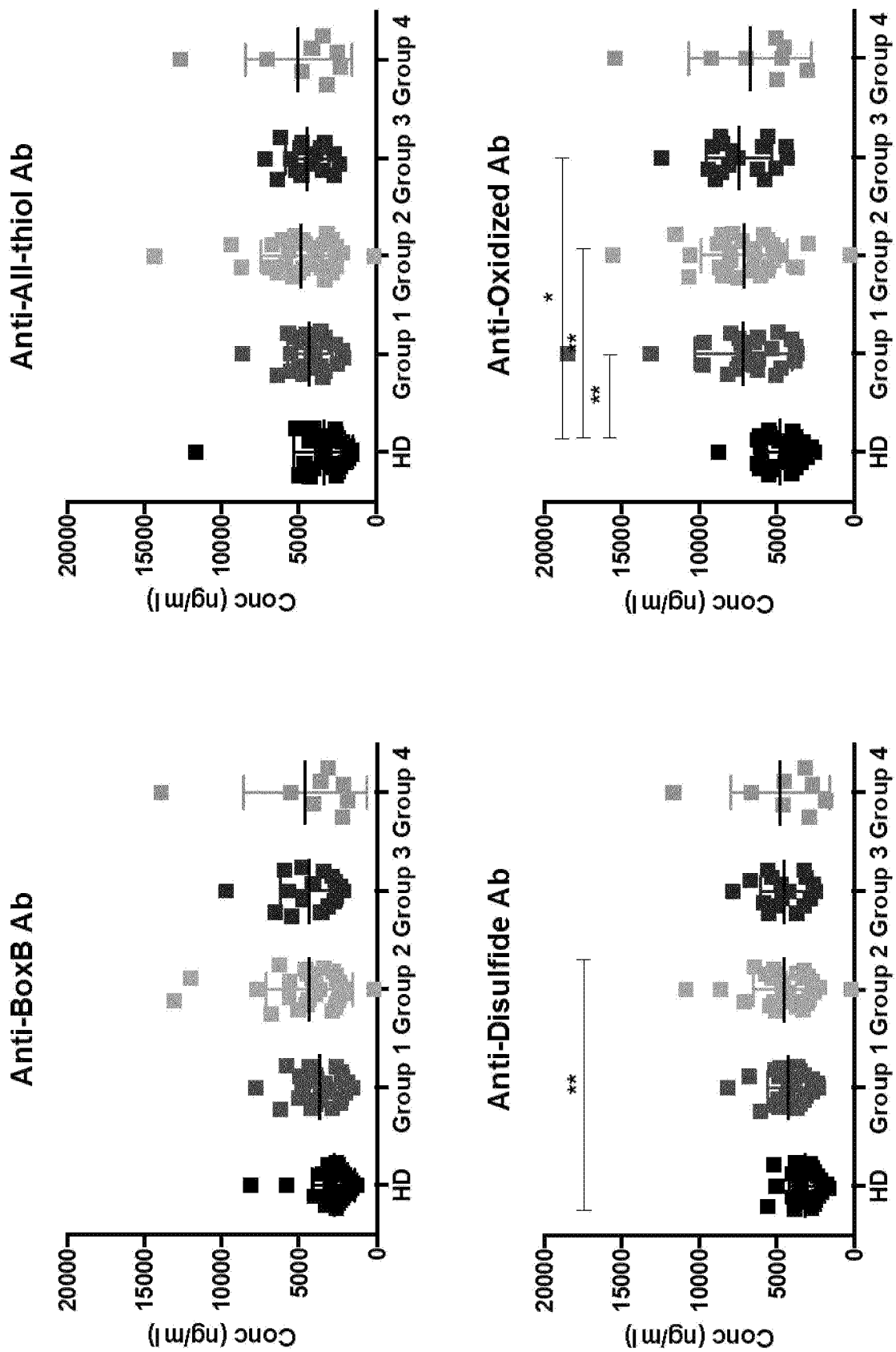
FIG. 16. Comparison of levels of specific antibodies for the different forms of HMGB1 in healthy donors (HD) and $HIV^+$ patients with neurological disorders. Plates were coated with 3 µg/ml of the indicated forms of HMGB1. 0.5 mM DTT was added to the coating buffer in order to obtain the all-thiol form. 100 mM $H_2O_2$ was added to the coating buffer in order to obtain the oxidized form of HMGB1. Titration of total specific antibodies for the different forms of HMGB1 was made in the serum of 29 HD and 68 HIV-infected patients. Groups of patients were defined according to their clinical neurological status (group 1: stage 1, no HAND, n=22; group 2: stage 2, no HAND with single deficit, n=26; group 3: stage 3, ANI, n=12; group 4: stage 4, MND+HAD, n=8). Statistical significance (two-sided Mann-Whitney test) is shown:*p<0.05, **p<0.01.
Figure 17:
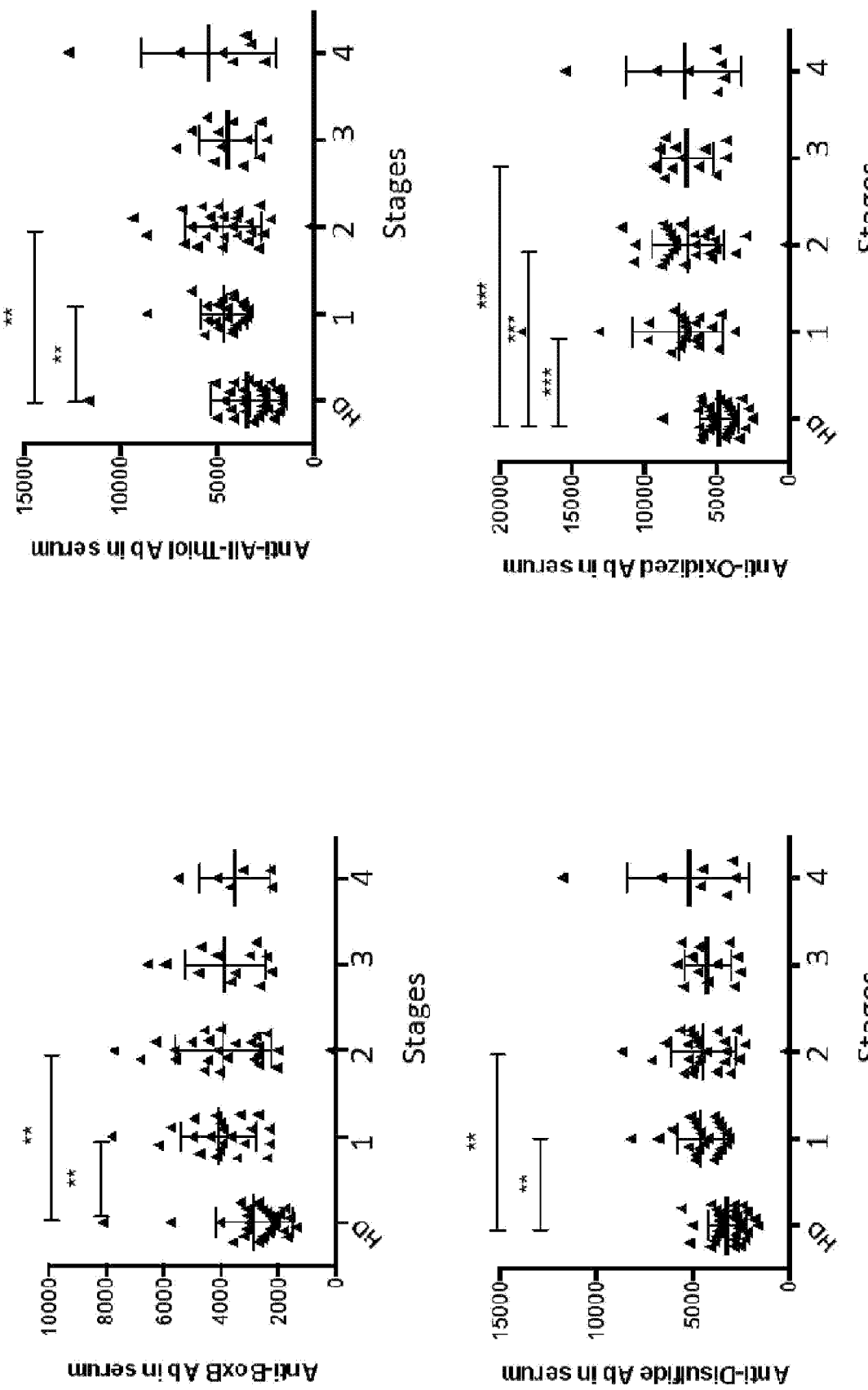
FIG. 17. Comparison of levels of IgG specific antibodies for the different forms of HMGB1 in healthy donors (HD) and HIV+ patients with neurological disorders. Concentrations of IgG antibodies (ng/ml) specific for the different redox forms of HMGB1 (all-thiol, disulfide, oxidized) and specific for Box B were determined in sera from 10 healthy donors (HD) and 103 HIV-1-infected patients according to the same protocol as the one described for FIG. 16. Groups of patients were defined according to their clinical neurological status confirmed by Magnetic Resonance Imaging (MRI). Stage 1: no HAND (n=37), stage 2: no HAND with single deficit (n=37); stage 3: ANI (n=16); stage 4: MND+HAD (n=13). Two-sided Mann-Whitney p values are: p<0.01; *p<0.001.

In FIGS. 16 and 17, the levels of antibodies specific for the different forms of HMGB1 were compared between the 5 groups of subjects.

In a first stratification of patients made according to their clinical neurological status (FIG. 16), no statistically significant differences were detected between the 5 groups for specific antibodies to all-thiol form of HMGB1 and for specific antibodies to Box B. The only antibodies that discriminated between patients and healthy donors were specific of the disulfide form of HMGB1 (Two-sided Mann-Whitney p value<0.01 for group 2) and of the oxidized form of HMGB1 (Two-sided Mann-Whitney p value<0.01 for groups 1 and 2 and p<0.05 for group 3).

A second stratification of patients was based on clinical neurological alterations confirmed with Magnetic Resonance Imaging (MRI) providing a more precise definition and distribution of the group of patients (FIG. 17). Using this medical imaging technology, some patients were reallocated a different stage of neurological impairment, which affected the obtained results against the first stratification of patients (FIG. 16). In this second stratification of patients (FIG. 17), the levels of IgG antibodies specific for the various forms of HMGB1 were statistically different between HD and stage 1, stage 2 patients (Two-sided Mann-Whitney p values <0.01 for anti-Box B Abs, anti-all-thiol Abs and anti-disulfide Abs, and two-sided Mann-Whitney p value <0.001 for anti-oxidized Abs). Thus, the levels of antibodies specific for the various forms of HMGB1 allowed the identification of very early stages of neurological impairment (stages 1 and 2). Moreover, anti-oxidized HMGB1 antibodies were kept elevated in stage 3 patients (two-sided Mann-Whitney p value<0.001), making antibodies specific for the oxidized form of HMGB1 the most robust biomarker of HAND stage of HIV infection.

Altogether, these observations should help to address the question of the distribution of these antibodies in pathological conditions, and the correlates with clinical evolution.

Figure 18:
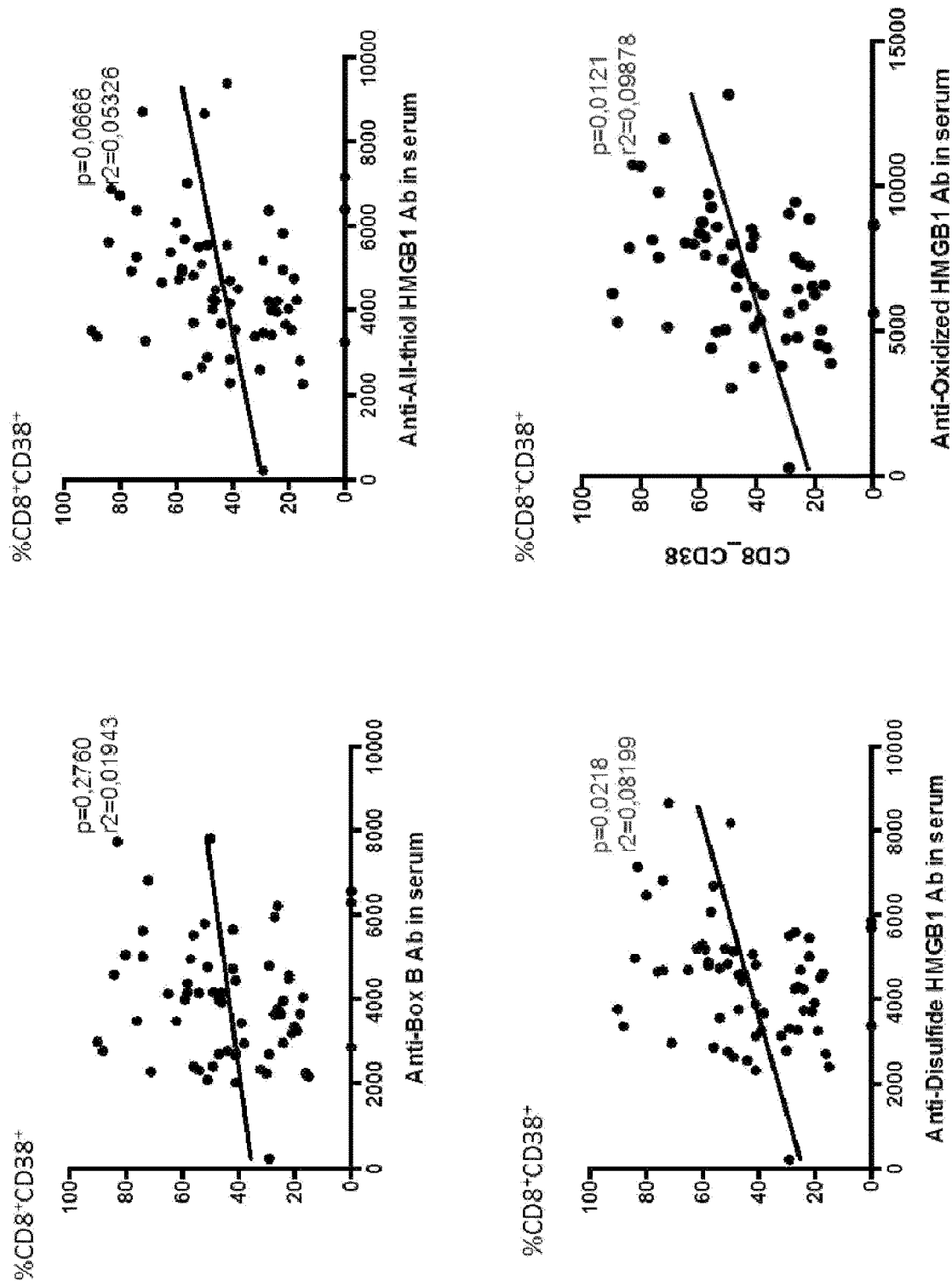
FIG. 18. Correlation between serum levels of IgG antibodies specific for the different forms of HMGB1 and immune activation (percentage of CD8+ CD38+ T cells). Spearman correlations between serum levels of antibodies specific for the different redox forms of HMGB1 and specific for Box B and percentages of CD8+ CD38+ T cells were calculated on sera from 73 HIV-infected patients. The coefficient of correlation ($r^2$) and p value are reported on each graph.

XII. Specific Antibodies to Disulfide and Oxidized HMGB1 Positively Correlate with Two Other Biomarkers of HIV Infection Whole blood from a cohort of 73 chronically HIV-infected patients was tested for the expression of the activation markers HLA-DR and CD38. Blood samples were stained within 8 h of blood draw. CD38 and HLA-DR expression was measured on CD4 and CD8 T cells by six-color flow cytometry using a whole blood cell procedure and monoclonal antibodies specific for CD3 coupled to fluorescein isothiocyanate (FITC), CD8 coupled to peridinin-chrorophyll-protein-cyanin 5.5 (PerCP-Cy5.5), CD4 coupled to phycoerythrin cyanin 7 (PC7), CD45 coupled to allophycocyanin 7 (APC-Cy7) and CD38 coupled to phycoerythrin (PE) and HLA-DR coupled to allophycocyanin (APC). Flow cytometric acquisition and analysis were performed on a FACSCanto flow cytometer and analysis was performed using FACSDiva software. Immune lymphocyte activation is shown by the increased expression of CD8$^+$ T cells expressing the activation marker CD38. Serum from these patients were tested for antibodies specific for the various forms of HMGB1. Spearman correlations (significance with p<0.05) show that the levels of anti-disulfide and anti-oxidized HMGB1 antibodies (ng/ml) were positively correlated with the % CD8+CD38+ T cells, a biomarker of generalized immune activation which characterize chronic HIV infection (FIG. 18).

Figure 19:
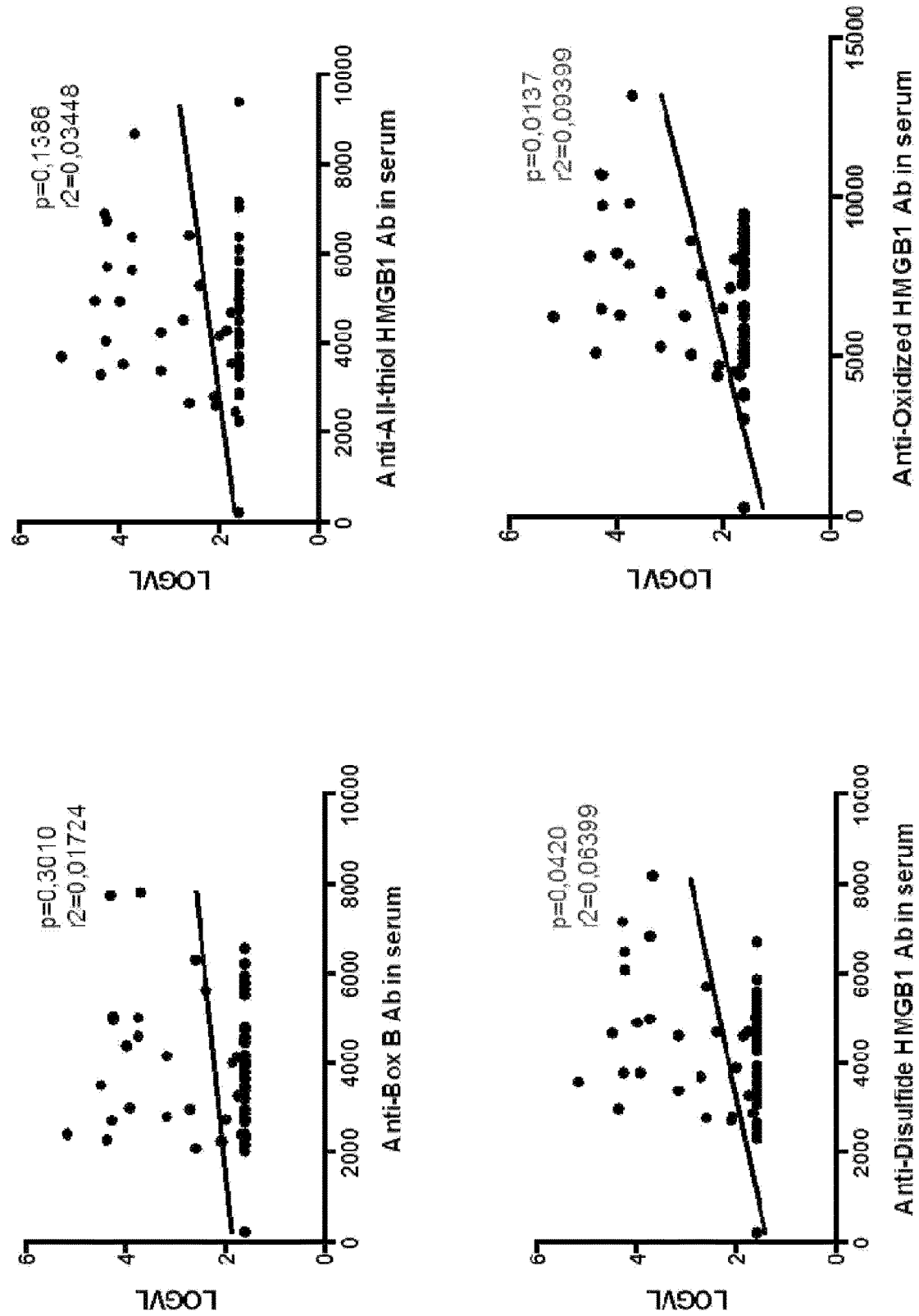
FIG. 19. Correlation between serum levels of antibodies specific for the different forms of HMGB1 and plasma viral load. Spearman correlations between serum levels of IgG antibodies specific for the different redox forms of HMGB1 and Box B and plasma HIV-1 RNA viral load (VL) were calculated on sera of 73 HIV-infected patients. The coefficient of correlation ($r^2$) and p value are reported on each graph.

In the same cohort of 73 chronically HIV-infected patients, quantification of plasma HIV-1 RNA viral load (VL) was performed by RT-PCR (Ampliprep/CobasTaqman Roche Molecular system), with a lower detection limit of 40 copies/ml (1.6 $\log_{10}$/ml). Some of the patients had undetectable VL. Spearman correlations between viral load and the concentrations of IgG antibodies (ng/ml) specific for the various forms are shown. Positive correlations (significance with $p<0.05$) were found for antibodies specific for disulfide and oxidized HMGB1 (FIG. 19).

Overall these findings indicated that IgG antibodies specific for the disulfide and oxidized HMGB1 forms, whose levels were statistically increased in very early stages of HIV-associated neurological impairment, were associated with persistent immune activation/inflammation of the CNS, due to persistent viral expression in the patient, albeit most of them were treated with antiretroviral therapy.

The invention claimed is:

1. An in vitro method for quantitating specific antibodies for at least one redox form of High mobility group box 1 (HMGB1) contained in a biological sample obtained from a subject comprising:
   a) contacting said biological sample with two redox forms of HMGB1; and
   b) quantitating the specific antibodies for the two redox forms of HMGB1;
   wherein the redox forms of HMGB1 are selected from the group of fully reduced HMGB1 in which all three cysteine residues at positions 23, 45 and 106 have been completely reduced to thiols, disulfide-HMGB1 having a disulfide bridge between cysteine residues at positions 23 and 45 and a reduced cysteine residue at position 106, and oxidized-HMGB1 in which the three cysteine residues at positions 23, 45 and 106 have been oxidized to sulfonates.

2. The in vitro method according to claim 1, comprising before the step of contacting the biological sample with the two redox forms of HMGB1, a step of treating the biological sample by an acid solution to dissociate the immune complexes found in the sample, wherein in said method, the quantitated specific antibodies for the two redox forms of HMGB1 are total specific antibodies for the two redox forms of HMGB1.

3. The in vitro method according to claim 1, wherein the quantitated specific antibodies for the two redox forms of HMGB1 are their circulating fraction (circulating antibodies) and/or their immunologically complexed fraction.

4. The in vitro method according to claim 1, wherein said at least one redox form of HMGB1 has a mammalian origin.

5. The in vitro method according to claim 1, wherein said biological sample is blood, plasma, serum, saliva, peripheral blood mononuclear cells (PBMCs) or PBMC supernatant, CerebroSpinal Fluid (CSF) and/or wherein said biological sample is diluted from 1/800 to 1/2000.

6. The in vitro method according to claim 1, wherein the quantities of specific antibodies for the two redox forms of HMGB1 are determined by ELISA using the two redox forms of HMGB1 coated on solid supports.

7. The in vitro method according to claim 6, wherein said method comprises the steps of:
   coating a solid support with at least one redox form of HMGB1, redox form of HMGB1 is oxidized HMGB1;
   washing the solid support;
   blocking unbound sites with a saturation buffer;
   optionally, treating the biological sample by an acid solution to dissociate the immune complexes found in the sample;
   adding the biological sample to said solid support;
   optionally, adding a secondary antibody having binding capacity for the quantitated antibodies in complex with a redox form of HMGB1;
   quantitating the specific antibodies for at least one redox form of HMGB1.

8. The in vitro method according to claim 1:
   for quantitating specific antibodies for fully reduced HMGB1, wherein the method comprises a step of treating fully reduced HMGB1 to stabilize the reduced state of HMGB1, said treatment encompassing adding a reducing agent to fully reduced HMGB1; or
   for quantitating specific antibodies for oxidized-HMGB1, wherein the method comprises a step of treating disulfide-HMGB1 to obtain oxidized-HMGB1, said treatment encompassing adding a reactive oxygen species (ROS)[,] to disulfide-HMGB1.

9. The in vitro method according to claim 1, comprising:
   individually quantitating specific antibodies for fully reduced HMGB1, disulfide-HMGB1 and oxidized-HMGB1;
   individually quantitating specific antibodies for oxidized HMGB1 and specific antibodies for fully reduced HMGB1; or
   individually quantitating specific antibodies for oxidized HMGB1 and specific antibodies for disulfide HMGB1.

10. The in vitro method of claim 1, wherein the sample is contacted with fully reduced HMGB1, disulfide-HMGB1 and oxidized-HMGB1.

* * * * *

UNITED STATES PATENT AND TRADEMARK OFFICE
CERTIFICATE OF CORRECTION

| | |
|---|---|
| PATENT NO. | : 11,460,473 B2 |
| APPLICATION NO. | : 15/771182 |
| DATED | : October 4, 2022 |
| INVENTOR(S) | : Marie-Lise Gougeon et al. |

It is certified that error appears in the above-identified patent and that said Letters Patent is hereby corrected as shown below:

On the Title Page

Item (54) and in the Specification, Column 1, Line 2:
Delete "AN".

In the Claims

Column 20:
Line 15, Claim 7, delete ", redox form of HMGB1 is oxidized HMGB1".

Column 20:
Line 37, Claim 8, delete "[,]".

Signed and Sealed this
Seventeenth Day of January, 2023

Katherine Kelly Vidal
*Director of the United States Patent and Trademark Office*